(12) United States Patent
Richard et al.

(10) Patent No.: US 6,240,929 B1
(45) Date of Patent: Jun. 5, 2001

(54) HETEROCYCLIC QUATERNARY POLYAMMONIUM SILICON POLYMERS AND THEIR USE IN COSMETIC COMPOSITIONS

(75) Inventors: Hervé Richard, Villepinte; Alain LaGrange, Coupvray, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/424,773

(22) PCT Filed: Mar. 23, 1999

(86) PCT No.: PCT/FR99/00679

§ 371 Date: Jan. 6, 2000

§ 102(e) Date: Jan. 6, 2000

(87) PCT Pub. No.: WO99/50338

PCT Pub. Date: Oct. 7, 1999

(30) Foreign Application Priority Data

Apr. 1, 1998 (FR) .................................................. 98 04059

(51) Int. Cl.$^7$ ............................... A45D 7/04; C08G 77/26
(52) U.S. Cl. .............................. 132/202; 528/28; 528/27; 556/413; 556/450; 556/425; 424/70.2; 424/70.51; 424/70.12; 424/70.6; 132/204; 132/208; 8/405; 524/800; 524/81
(58) Field of Search ..................................... 556/413, 450, 556/425; 528/27, 28; 424/70.2, 70.51, 70.12, 70.6; 132/202, 204, 208; 8/405; 524/800, 81

(56) References Cited

U.S. PATENT DOCUMENTS

| | | |
|---|---|---|
| 4,533,714 | 8/1985 | Sebag et al. . |
| 4,587,321 | 5/1986 | Sebag et al. . |
| 4,749,732 | 6/1988 | Kohl et al. . |
| 4,833,225 | 5/1989 | Schaefer et al. . |
| 5,302,684 | * 4/1994 | Stapp et al. . |

FOREIGN PATENT DOCUMENTS

| | | |
|---|---|---|
| 0 227 994 | 7/1987 | (EP) . |
| 0 282 720 | 9/1988 | (EP) . |
| 0 295 780 | 12/1988 | (EP) . |
| 0 714 954 | 6/1996 | (EP) . |
| 1 530 369 | 5/1968 | (FR) . |
| 2 535 730 | 5/1984 | (FR) . |
| 2 673 179 | 8/1992 | (FR) . |
| 2 197 352 | 5/1988 | (GB) . |
| WO 92/05764 | 4/1992 | (WO) . |
| WO 94/07844 | 4/1994 | (WO) . |
| WO 95/01772 | 1/1995 | (WO) . |
| WO 95/15144 | 6/1995 | (WO) . |

OTHER PUBLICATIONS

J. Torres et al., "Synthesis and Physicochemical Studies on 1,2–Bisazolylethanes", Journal of Heterocyclic Chemistry, vol. 25, No. 3, 1988, pp. 771–782.

Ying–Hung So, "Novel Thermoset Polyimidazole Amides", Macromolecules, vol. 25, No. 2, Jan. 20, 1992, pp. 516–520.

Kristi J. Robson et al., "6–Hydroxy–4–Sphingenine in Human Epidermal Ceramides", Journal of Lipid Research, vol. 35, No. 11, Nov. 1994, pp. 2060–2068.

Cheng He Zhou et al., "Convenient and Efficient Synthesis of Bis–Imidazoles", Chinese Chemical Letters, vol. 7, No. 4, 1996, pp. 321–324.

English language Derwent Abstract of EP 0 714 954.

English language Derwent Abstract of FR 1 530 369.

English language Derwent Abstract of FR 2 673 179.

* cited by examiner

*Primary Examiner*—Robert Dawson
*Assistant Examiner*—Kuo-Liang Peng
(74) *Attorney, Agent, or Firm*—Finnegan, Henderson, Farabow, Garrett & Dunner

(57) ABSTRACT

The invention relates to novel polymers containing at least some units of formula (I):

$$\left[ A_1^{\oplus} - B_1 - A_2^{\oplus} - B_2 - \underset{R_2}{\overset{R_1}{\underset{|}{\overset{|}{Si}}}} - \left[ O - \underset{R_4}{\overset{R_3}{\underset{|}{\overset{|}{Si}}}} \right]_p - B_2 - \right] \quad (I)$$
$$X^{\ominus} \quad X^{\ominus}$$

in which:

$A_1^{\oplus}$ and $A_2^{\oplus}$; which may be identical or different, denote:
  a) a quaternary unsaturated heterocycle; or
  b) a quaternary ammonium and at least one of the groups $A_1^{\oplus}$ and $A_2^{\oplus}$ denotes a quaternary unsaturated heterocycle;

p denotes an integer or fraction from 0 to 50;

$B_1$ denotes an α, ω-bis(alkyl)polysiloxane group or a linear or branched, saturated or unsaturated hydrocarbon-based chain containing upto 6 consecutive carbon atoms, which can contain one or more hydroxyl groups and can be interrupted by one or more oxygen atoms and/or several aromatic rings;

$B_2$ denotes a linear or branched, saturated or unsaturated hydrocarbon-based chain containing upto 6 consecutive carbon atoms, which can contain one or more hydroxyl groups and can be interrupted by one or more oxygen atoms and/or several aromatic rings;

$R_1$, $R_2$, $R_3$ and $R_4$, which may be identical or different, denote a $C_1$–$C_6$ alkyl radical or a phenyl radical;

$X^{\ominus}$ denotes an anion derived from an inorganic or organic acid; and to their use in cosmetics.

57 Claims, No Drawings

HETEROCYCLIC QUATERNARY POLYAMMONIUM SILICON POLYMERS AND THEIR USE IN COSMETIC COMPOSITIONS

The present invention relates to novel heterocyclic polyquaternary ammonium silicone polymers, to cosmetic compositions using them and to processes for treating keratin fibres, and in particular the hair using these polymers.

It has already been proposed to use polyquaternary polysiloxane polymers in order to improve the disentangling of the hair. Such compositions are described in particular in French patent No. 2,535,730 by the Applicant.

Document U.S. Pat. No. 4,833,225 describes polyquaternary polysiloxane polymers which are resistant to removal by washing and allow easy styling.

Cationic polymers have a great affinity for keratin fibres, such as the hair, on account of the interaction of the cationic groups with the anionic groups of the hair.

These polymers become deposited on the hair all the more easily the more sensitized this hair, and their affinity for the hair is often such that they are resistant to removal by shampooing or brushing.

It is found, however, that although the use of such cationic polymers has many advantages, since they facilitate disentangling of the hair and they give the hair liveliness and a shiny appearance, on account of their affinity for keratin, these polymers have a tendency to accumulate on the hair after repeated applications.

Moreover, cationic polymers containing quaternary groups often have the drawback of being incompatible with anionic surfactants, which reduces the possibilities for use and imposes their use in two-stage treatments, before or after shampooing.

The Applicant has discovered that certain polyquaternary ammonium silicone polymers, which do not have the above-mentioned drawbacks, containing at least some unsaturated quaternary heterocycles, are particularly advantageous for treating keratin fibres, and in particular human keratin fibres such as the hair.

The Applicant has discovered, in particular, that the use of these polymers allows keratin fibres, and in particular human keratin fibres such as the hair, to be protected both against attack due, in particular, to sunlight, to bad weather and to perspiration, and against attack resulting from treatment of keratin fibres, and in particular human keratin fibres such as the hair, such as, for example, bleaching, permanent-waving or dyeing operations.

It has been found that keratin fibres have a tendency to become brittle when they are subjected to these treatments; keratin fibres, and in particular human keratin fibres such as the hair, become dry, dull, coarse and difficult to disentangle and to style.

The protective agents of the invention are used in particular in any cosmetic process which includes at least one step during which the keratin fibres are liable to be exposed to various attacking factors, and thus allow the abovementioned drawbacks to be avoided.

These protective agents can be applied to the keratin fibres during, prior to or subsequent to this step during which the keratin fibres are subjected to attacking factors.

Preferably, the protective agents of the present invention are used in a process during which at least one application of an alkaline composition onto the keratin fibres takes place.

A subject of the invention is thus novel heterocyclic polyquaternary silicone polymers.

A subject of the invention is also the use of these novel heterocyclic polyquaternary silicone polymers as agents for protecting keratin fibres.

A subject of the invention is also cosmetic compositions using them, and in particular compositions intended for permanently shaping keratin fibres, bleaching compositions and dye compositions.

A subject of the invention is also processes for treating keratin fibres, and in particular human keratin fibres such as the hair, using these compositions.

Other subjects of the present application will become apparent on reading the description and the examples which follow.

The polymers of the present invention contain at least some repeating units of formula (I):

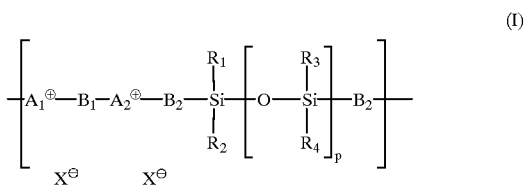

in which:

$A_1^{\oplus}$ and $A_2^{\oplus}$; which may be identical or different, denote:

a) a quaternary unsaturated heterocycle of formula (II):

in which

E, G, L and J, which may be identical or is different, denote a carbon, oxygen, sulphur or nitrogen atom, at least one denoting a nitrogen atom;

E, G, L and J can be substituted, when one or more of these atoms denote a carbon atom, with one or more halogen atoms, hydroxyl, nitro, cyano, sulphydryl or carboxyl groups, alkyl, monohydroxyalkyl, polyhydroxyalkyl, thioalkyl, cyanoalkyl, alkoxy, acyl or acetyloxy groups, or substituted or unsubstituted cycloalkyl groups or substituted or unsubstituted alkylaryl groups, or with one or more groups —$NHR_N$ in which, $R_N$ denotes an acetyl or ureido group;

when E, G, L or J denote a third nitrogen atom, this can be substituted with a hydrogen, an alkyl, monohydroxyalkyl, polyhydroxyalkyl or substituted or unsubstituted aryl radical or a substituted or unsubstituted alkylaryl radical;

the substituents of two of the atoms E, G, L and J can also form, together with the atoms to which they are attached, a substituted or unsubstituted 5- to 7-membered aromatic ring; or b) a quaternary ammonium of formula (III)

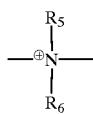
(III)

in which:

R$_s$ and R$_6$, which may be identical or different; denote a carbdixyl group, an alkyl, polyhydroxyalkyl, thioalkyl, cyanoalkyl, alkoxy, acyl or acetyloxy group, a substituted or unsubstituted cycloalkyl, substituted or unsubstituted aryl or substituted or unsubstituted alkylaryl group or a group —NHR$_N$ in which R$_N$, denotes an acetyl or ureido group;

R$_5$ and R$_6$ can also form, together with the nitrogen atom to which they are attached, a saturated ring of 5 to 7 carbon members;

and at least one of the groups A$_1^\oplus$ and A$_2^\oplus$ denotes a quaternary unsaturated heterocycle of formula (II);

p denotes an integer or fraction from 0 to 50 and preferably from 0 to 10; p can represent a defined number or an average statistical value;

B$_1$ denotes an α, ω-bis(alkyl)polysiloxane group or a linear or branched, saturated or unsaturated hydrocarbon-based chain containing upto 6 consecutive carbon atoms, which can contain one or more hydroxyl groups and can be interrupted by one or more oxygen atoms and/or several aromatic rings;

B$_2$ denotes a linear or branched, saturated or unsaturated hydrocarbon-based chain containing upto 6 consecutive carbon atoms, which can contain one or more hydroxyl groups and can be interrupted by one or more oxygen atoms and/or one or more aromatic rings;

R$_1$, R$_2$, R$_3$ and R$_4$, which may be identical or different, denote a C$_1$–C$_6$ alkyl radical or a phenyl radical;

X$^\ominus$ denotes an anion derived from an inorganic or organic acid.

In the context of the present invention:

The halogen atoms preferably denote a fluorine, chlorine, bromine or iodine atom.

The alkyl, monohydroxyalkyl and polyhydroxyalkyl radicals and the hydrocarbon-based gruops can be linear or branched.

The alkyl groups denote, in particular, groups containing from 1 to 20 carbon atoms, such as, for example, methyl, ethyl, propyl, isopropyl, n-propyl, butyl, n-butyl, tert-butyl, pentyl, n-pentyl, isopentyl, n-hexyl, isohexyl, heptyl, octyl, nonyl, decyl, undecyl, dodecyl and pentadecyl groups. Preferably, the alkyl groups denote a group containing from 1 to 6 carbon atoms.

Among the hydrocarbon-based groups, mention may be made of polymethylene groups containing from 1 to 20 carbon atoms.

Preferably, the hydrocarbon-based groups denote polymethylene groups containing from 2 to 8 carbon atoms.

The hydrocarbon-based groups can contain, attached to or inserted in the main chain, one or more aromatic rings, one or more oxygen, sulphur or nitrogen atoms, or one or more —SO—, —SO$_2$—, —SO$_3$H, amino, alkylamino, hydroxyl, quaternary ammonium or ureido groups.

Among the monohydroxyalkyl groups, mention may be made in particular of hydroxymethyl, hydroxyethyl, hydroxypropyl and hydroxybutyl groups.

Among the polyhydroxyalkyl radicals, mention may be made, for example, of dihydroxyethyl, dihydroxypropyl, trihydroxypropyl and dihydroxybutyl radicals.

The thioalkyl radicals denote a group —R—SH, R representing an alkyl group as defined above.

The cyanoalkyl radicals denote a group —R—C≡N, R representing an alkyl group as defined above.

The alkoxy groups denote a group —O—R, R representing an alkyl group as defined above.

The acyl groups denote a group —OC—R, R representing an alkyl group as defined above.

The acetyloxy groups denote a group —O—CO—R, R representing an alkyl group as defined above.

Among the cycloalkyl radicals, mention may be made in particular of cyclohexyl and cyclopentyl.

Among the aryl radicals, mention may be made in particular of phenyl or naphthyl groups.

Among the alkylaryl groups, mention may be made in particular of the benzyl, phenethyl or naphthylmethyl group.

Among the 5- to 7-membered aromatic rings, mention may be made, for example, of the aryl and alkylaryl rings mentioned above. The preferred aromatic rings are phenyl, pyrimidine, pyridine, pyrrole and pyrazole rings.

In the context of the present invention, the cycloalkyl radicals and the aromatic rings can be substituted with one or more halogen atoms or hydroxyl, amino or C$_1$–C$_6$ alkyl or hydroxyalkyl groups.

X$^\ominus$ represents, in particular, an anion derived from a halgoen such as chlorine, bromine, fluorine or iodine, an anion derived from inorganic acids such as phosphoric acid or sulphuric acid or an anion derived from an organosulphonic or organocarboxylic acid, in particular an alkanoic acid containing from 1 to 12 carbon atoms, such as acetic acid, a phenylalkanoic acid such as phenylacetic acid, benzoic acid, citric acid or para-toluenesulphonic acid. Preferably, X$^\ominus$ represents an anion derived from a halogen and even more preferably X$^\ominus$ represents a chloride or bromide anion.

In one preferred embodiment of the present invention, A$_1^\oplus$, and/or A$_2^\oplus$ represents a heterocycle of formula (II) containing two nitrogen atoms and three carbon atoms.

In another preferred embodiment of the present invention, at least one of the groups A$_1^\oplus$ or A$_2^\oplus$ denotes ternary imidazole group of formula (IV):

(IV)

in which

R$_7$, R$_8$, and R$_9$, which may be identical or different, denote a hydrogen or halogen atom, a hydroxyl, nitro, cyano, sulphydryl or carboxyl group, an alkyl, monohydroxyalkyl, polyhydroxyalkyl, thioalkyl, cyanoalkyl, alkoxy, acyl or acetyloxy group, a cycloalkyl, aryl or alkylaryl group or a group —NHR$_N$ in which R$_N$ denotes an acetyl or ureido group; the radicals R$_8$ and R$_9$ can also form, together with the atoms to which they are attached, a 5- to 7-membered aromatic ring.

In another embodiment of the present invention, at least one of the groups $A_1^\oplus$, or $A_2^\oplus$ denotes a quaternary pyrazole group of formula (V):

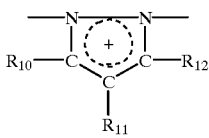
(V)

in which:

R$_{10}$, R$_{11}$ and R$_{12}$ which may be identical or different, denote a hydrogen or halogen atom, a hydroxyl, nitro, cyano, sulphydryl or carboxyl group, an alkyl, monohydroxyalkyl, polyhydroxyalkyl, thioalkyl, cyanoalkyl, alkoxy, acyl or acetyloxy group, a cycloalkyl, aryl or alkylaryl group or a group —NHR$_N$ in which R$_N$ denotes an acetyl or ureido group;

two of the radicals R$_{10}$, R$_{11}$ or R$_{12}$ can also form, together with the atoms to which they are attached, a 5- to 7-membered aromatic ring.

In another preferred embodiment of the present invention, the groups $A_1^\oplus$, and $A_2^\oplus$ simultaneously denote a quaternary imidazole group of formula (IV), in which R$^7$, R$^8$ and R$^9$, which may be identical or different, denote a hydrogen atom, a hydroxyl, nitro, cyano, sulphydryl or carboxyl group, an alkyl, monohydroxyalkyl or polyhydroxyalkyl group; radicals R$_8$ and R$_9$ can also form, together with the atoms to which they are attached, a 5- to 7-membered aromatic ring;

In another particularly preferred embodiment of the present invention, the groups $A_1^\oplus$ and $A_2^\oplus$ simultaneously denote a quaternary imidazole group of formula (IV) in which R$_7$, R$_8$ and R$_9$, which may be identical or different, denote a hydrogen atom or a C$_1$ to C$_6$ alkyl group and the radicals R$_8$ and R$_9$ can form, together with the atoms to which they are attached, a phenyl ring.

In another preferred embodiment of the present invention, $A_1^\oplus$ represents a quaternary ammonium of formula (III) in which R$_5$ and R$_6$, which may be identical or different, denote a hydrogen atom or a C$_1$ to C$_6$ alkyl group, or form, together with nitrogen, a 6-membered group and $A_2^\oplus$ denotes a quaternary imidazole group of formula (IV) in which R$_7$, R$_8$ and R$_9$, which may be identical or different, denote a hydrogen atom or a C$_1$–C$_6$ alkyl and the radicals R$_8$ and R$_9$ can also form, together with the atoms to which they are attached, a phenyl ring.

In another preferred embodiment of the invention, B$_1$ denotes a group chosen from the following groups:

i) —(CH$_2$)$_n$— with n denoting an integer from 2 to 6
ii) —CH$_2$—CH═CH—CH$_2$—
iii) —CH$_2$—C≡C—CH$_2$—
iv) —CH(CH$_3$)—(CH$_2$)$_2$—
v) —CH$_2$CHOH—CH$_2$—
vi)—[CH$_2$—CH$_2$—O]$_x$—CH$_2$—CH$_2$— with x=1–15 vii)

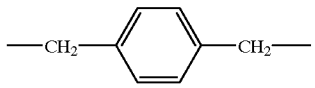

viii)

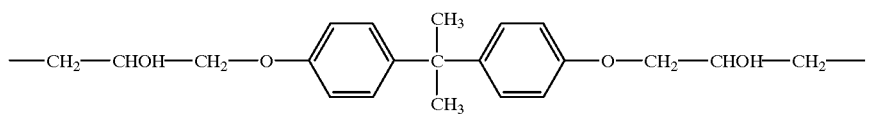

ix)

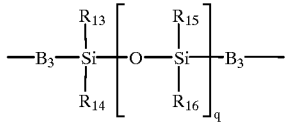

in which R$_{13}$, R$_{14}$, R$_{15}$ and R$_{16}$, which may be identical or different, denote a C$_1$—C$_6$ alkyl radical or a phenyl radical, q denotes an integer or fraction from 0 to 50 preferably from 0 to 10, and B$_3$ denotes B$_2$ or —(CH$_2$)$_t$— with t denoting an integer from 1 to 6.

In one preferred embodiment of the invention, B$_2$ denotes a group —(CH$_2$)$_m$— it which m is an integer from 1 to 6 and preferably from 1 to 4.

Preferably, in the polymers mentioned above, X$^\oplus$ represents a halide, and more particularly Cl$^-$ or Br$^-$ and R$_1$, R$_2$, R$_3$ and R$_4$ denote a methyl radical.

Polymers which are particularly preferred are the polymers corresponding to formula (I) in which $A_1^\oplus$ and $A_2^\oplus$ simultaneously denote a quaternary group of formula (IV) with R$_7$=R$_8$=R$_{9=H, B1}$ denotes —(CH$_2$)$_n$— in which n is an integer from 2 to 6 or

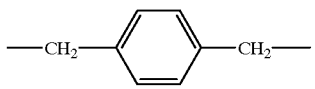

B$_2$ denotes —(CH$_2$)$_m$— in which m is an integer from 1 to 4, p is an integer from 0 to 4, R$_1$=R$_2$=CH$_3$ where p=0 and R$_1$=R$_2$=R$_3$=R$_4$=CH$_3$ when p>0 and X$^\ominus$ represents a chloride or bromide anion.

The polymers of the present invention preferably have an average molecular weight of between 1000 and 20,000 measured by gel permeation chromatography taking polyethylene glycol as reference.

The compounds of the present invention are synthesized in two steps. The first step consists in synthesizing the diamine and the second step consists either in quaternizing the diamine in the presence of a dihalide or a disulphonate, or in condensing the diamine with a diepoxide in the presence of an inorganic or organic acid.

The diamine is synthesized by reacting the corresponding diazole with a dihalide or disulphonate in a solvent, in the presence of a base, at a temperature of between room temperature and the reflux point.

These solvents can be water, aromatics such as benzene or toluene, dimethyl sulphoxide, tetrahydro-furan or dimethylformamide.

These solvents can also be used as a mixture.

The bases can consist of hydroxides such as sodium hydroxide or potassium hydroxide, or of amides, carbonates, or hydrides.

This synthesis can also take place by phase transfer by adding a phase transfer catalysts.

Synthesis are described in particular in the documents J. Elguero et al., Journal of Heterocyclic Chemistry 25, 771–782 (1988), Yin-hung So, Macromolecules 25, 516–520 (1992) and R. G. Xie et al., Chinese Chemical Letters 7, 321–324 (1996).

The quaternization with a dihalide or a disulphonate is carried out according to the following scheme:

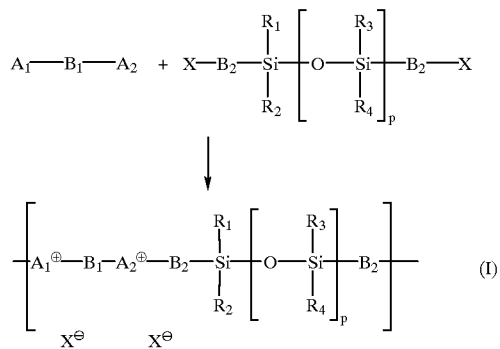

in which $A_1^\oplus$, $A_2^\oplus$, $B_1$, $B_2$, $R_1$, $R_2$, $R_3$, $R_4$, $X^\ominus$ and p have the same meaning as above.

It is carried out in a solvent at a temperature of between room temperature and the reflux point. The solvents can be chosen from water, alcohols, aromatics, such as benzene or toluene, or tetrahydrofuran. These solvents can also be used as a mixture. Preferably, they are chosen from water, alcohols and aqueous-alcoholic mixtures.

The condensation of the diamine with a diepoxide in the-presence of an inorganic or organic acid takes place according to the following scheme:

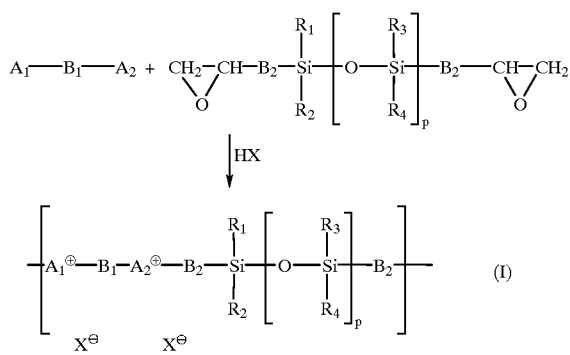

in which $A_1^\oplus$, $A_2^\oplus$, $B_1$, $B_2$, $R_1$, $R_2$, $R_3$, $R_4$, $X^\ominus$ and p have the same meaning as above.

This condensation is carried out in the presence of 2 equivalents of acid HA relative to the diamine, and at temperatures of between 40° C. and 120° C. and in an aqueous-alcoholic solvent.

A subject of the present invention is, in particular, the cosmetic use of a polymer as defined above.

A subject of the present invention is also the use, as an agent for protecting keratin fibres, of a polymer containing at least some repeating units of formula (I) as defined above.

A subject of the presenty invention is also compositions intended for the cosmetic treatment of keratin fibres, and in particular of the hair, containing at least one polymer containing at least some repeating units of formula (I) as defined previously.

These compositions generally contain from is 0.01 to 10% by weight of polymer, and preferably from 0.2 to 5%.

The cosmetic compositions according to the invention can be aqueous or aqueous-alcoholic, solvent-based and optionally contain oils and can be in the form of solutions, lotions, creams, dispersions, gels or aerosols.

The cosmetic compositions according to the invention can contain, in addition to polymer consisting of at least some repeating units of formula (I), any component used in cosmetic compositions, in particular anionic, cationic, amphoteric, zwitterionic or nonionic surfactants, foam synergists, foam stabilizers, opacifiers, sequestering agents, thickeners, emulsifiers, softeners, preserving agents, protein derivatives, natural substances, dyes, fragrances and anionic, cationic, amphoteric and nonionic polymers.

Another subject of the invention consists of a cosmetic treatment process for keratin fibres, in particular the hair, in which a cosmetic composition as defined above is applied to the keratin fibres.

The polymers consisting of at least some repeating units of formula (I) of the present invention are used in particular in compositions used for the permanent reshaping of keratin fibres, in particular the hair, or in dye compositions or bleaching compositions, which constitute another subject of the invention.

The most common technique for permanently reshaping keratin fibres consists, in a first stage, in applying a composition containing a reducing agent to the keratin fibres and then, in a second stage, in applying, to the keratin fibres which have been placed under tension beforehand by curlers or other means, an oxidizing composition so as finally to give the keratin fibres the desired shape.

The polymers of the present invention can be contained in the reducing and/or oxidizing composition.

The reducing compositions in accordance with the invention comprise, in a medium which is suitable for permanently reshaping keratin fibres, at least one reducing agent capable of breaking the disulphide linkages in keratin fibres, and at least one heterocyclic polyquaternary ammonium silicone polymer as defined above.

The reducing agents are generally chosen from sulphites, bisulphites and thiols.

Among the preferred reducing agents, mention may be made of cysteine and cysteamine and derivatives thereof such as the cosmetically acceptable salts thereof, for instance the hydrochlorides, hydrobromides, citrates, acetates and sulphates, thiolactic acid, thioglycolic acid and the cosmetically acceptable esters thereof, in particular glyceryl thioglycolate.

The reducing agents are present in proportions which are sufficient to reduce the disulphide linkages of keratin, preferably between 1 and 25% and in particular between 1 and 10% by weight.

The polymers of the present invention can be present in proportions of between 0.01% and 10% by weight of the reducing composition, and preferably between 1% and 5%.

The pH of the reducing compositions is adjusted so as to obtain a pH of between 6.5 and 11.5.

The alkaline agents are preferably chosen from monoethanolamine, diethanolamine, triethanolamine, isopropanolamine, 2-methylamino-1-propanol, 1,3-propanediamine, an ammonium or alkali metal carbonate or bicarbonate, aqueous ammonia, an organic carbonate such as guanidine carbonate, or an alkali metal hydroxide, used alone or as a mixture.

This reducing composition can also contain nonionic, anionic, cationic or amphoteric surfactants, commonly used in such compositions. Among these, mention may be made of alkyl sulphates, alkylbenzene sulphates, alkyl ether sulphates, alkyl sulphonates, quaternary ammonium salts, alkylbetaines, oxyethylenated alkylphenols, alkylpolyglucosides, fatty acid alkanolamides, oxyethylenated fatty acid esters and nonionic surfactants of the hydroxypropyl ether family.

These surfactants are generally used in maximum proportions of 30%, and preferably between 0.5 and 10%, by weight relative to the total weight of the composition.

These compositions can also contain thickeners such as guar gum, tara gum or spruce meal.

These compositions can also contain treating agents such as volatile or non-volatile, linear or cyclic silicones or mixtures thereof. Among the silicones, mention may be made of polydimethylsiloxanes, quaternized polyorganosiloxanes as described in FR-A-2,535,730, polyorganosiloxanes containing an aminoalkyl group, which are modified with alkoxycarbonylalkyl groups, as described in patent U.S. Pat. No. 4,749,732, polyorganosiloxanes such as polydimethylsiloxane-polyoxyalkyl copolymers such as dimethicone copolyol, a polydimethylsiloxane containing stearoxy (stearoxydimethicone) end groups, a polydimethylsiloxane dialkylammonium acetate copolymer or a poly-dimethylsiloxane polyalkylbetaine copolymer described in GB-A-2,197,352, polysiloxanes organomodified with mercapto or mercaptoalkyl groups as described in FR-B-1,530, 369 and EP-A-0,295,780, as well as silanes such as stearoxytrimethylsilane.

Other ingredients which can be used in the reducing compositions containing the polymers of the invention are chosen from waxes, polymers chosen from cosmetically acceptable anionic, cationic ocher than those of the invention, nonionic or amphoteric polymers, swelling agents and penetration agents for reinforcing the efficacy of the reducing agent, such as dimethylisosorbitol, urea and its derivatives, pyrrolidone, n-alkylpyrrolidones, thiamorpholinone, alkyl ethers of alkylene glycol or of dialkylene glycol, such as, for example, propylene glycol monomethyl ether or dipropylene glycol monomethyl ether, $C_3$–$C_6$ alkanediols such as 1,2-propanediol, 2-imidazolidinone, as well as other compounds such as fatty alcohols, lanolin derivatives, ceramides, in particular the ceramides themselves, glycoceramides and pseudoceramides described in particular in FR-A-95/12399and in Downing, Journal of Lipid Research, Vol. 35, p. 2060, 1994, or in FR-A-2,673,179, EP-A- 0,227,994, WO-94/07844 and WO-92/05764, active ingredients such as pantothenic acid, panthenol, agents for preventing hair loss, antidandruff agents, suspension agents, sequestering agents, opacifiers, dyes and silicone or non-silicone sunscreens, as well as fragrances and preserving agents.

The silicone polymers of the present invention can also be present in oxidizing compositions used during the permanent shaping of keratin fibres. A subject of the invention is thus also an oxidizing composition for the permanent shaping of keratin fibres, which comprises, in a medium which is suitable for permanent-waving, at least one oxidizing agent and at least one polymer as defined above.

The oxidizing agents can be chosen from aqueous hydrogen peroxide solution, urea peroxides, bromates such as alkaline bromates, persalts or a mixture of alkaline bromates and a persalt.

When the oxidizing agent consists of aqueous hydrogen peroxide solution, it is present in proportions of between 1 and 10 volumes, and preferably of about 8 volumes.

When bromates are used, the concentration of alkaline bromates is from 1 to 12% and that of persalts is from 0.1 to 15% by weight relative to the total weight of the oxidizing composition.

The protective agents of the present invention can be present in proportions of between 0.01% and 10% by weight of the oxidizing composition, and preferably between 1% and 5% by weight.

The pH of these compositions is usually between 2 and 9 and preferably between 3 and 8; it is preferably acidic.

When aqueous hydrogen peroxide solution is used, it can be stabilized with phenacetin, acetanilide, monosodium and trisodium phosphates or with 8-hydroxyquinoline sulphates.

Another subject of the invention is a process for permanently shaping keratin fibres, and in particular the hair, which is essentially characterized in that:

a composition for reducing keratin is applied to the keratin fibres, which are preferably wet, the reducing composition being applied to the shaped fibres, after leaving on the fibres for a period which is sufficient to reduce the keratin, an oxidizing composition is applied, after leaving on the fibres for a period which is sufficient to fix the fibres; which were shaped and reduced during the first step, in a permanent shape, the fibres are rinsed, preferably with water; the reducing composition and/or the oxidizing composition being as defined above.

The keratin fibres are shaped by various means such as rollers, clips, bands with hooks, or simply by hand.

Another subject of the present invention is a composition for the direct dyeing of keratin fibres, and in particular human keratin fibres such as the hair, which comprises, in a medium which is suitable for dyeing, at least one polymer as defined above and at least one direct dye.

Among the direct dyes conventionally used, mention may be made of nitrobenzene dyes, such as nitrophenylenediamines, nitrodiphenylamines, nitroanilines, nitrophenyl ethers or nitrophenols, nitropyridines, anthraquinone dyes, mono- or diazo dyes, triarylmethane dyes, azine dyes, acridine dyes and xanthene dyes or alternatively metal-containing dyes.

The direct dyes more particularly preferred according to the invention are chosen from the following:

i) the nitrobenzene dyes of formula (A) below:

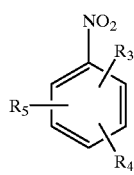

(A)

in which $R_3$ denotes an $NH_2$ radical, an amino radical monosubstituted with an alkyl, monohydroxyalkyl, polyhydroxyalkyl or aminoalkyl radical, or an amino radical disubstituted with identical or different alkyl, mono- or polyhydroxyalkyl or aminoalkyl radicals, $R_4$ denotes hydrogen, hydroxyl, alkoxy, mono- or polyhydroxyalkyloxy or the same meanings denoted above for $R_3$, except for a disubstituted amino radical, $R_5$ denotes hydrogen, alkyl, nitro or halogen,
ii) the anthraquinone dyes of formula (B) below:

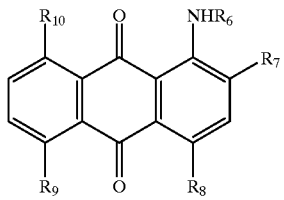
(B)

in which $R_6$ denotes hydrogen or a monohydroxyalkyl or polyhydroxyalkyl radical, $R_7$ denotes hydrogen or an alkyl or alkoxy radical, $R_8$ denotes hydrogen or a hydroxyl, amino, is monohydroxyalkylamino or polyhydroxyalkylamino radical, $R_9$ and $R_{10}$, which may be identical or different, are hydrogen, hydroxyl or amino, iii) the azo dyes of formula (C) below:

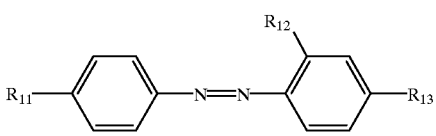
(C)

in which:

$R_{11}$, denotes a nitro or amino radical or an amino radical mono- or disubstituted with alkyls, $R_{12}$ denotes hydrogen or an alkyl radical, $R_{13}$ denotes an amino radical or an amino radical mono- or disubstituted with monohydroxyalkyls, it being understood that the alkyl and alkoxy radicals mentioned above in the formulae (A), (B) and (C) are $C_1$–$C_4$ and that they can be linear or branched, and the cosmetically acceptable salts of all of these compounds.

The term "$C_1$–$C_4$ alkyl" means in particular the methyl, ethyl, n-propyl, isopropyl, n-butyl, sec-butyl and tert-butyl radicals.

The term "cosmetically acceptable salts" more particularly denotes the hydrochlorides, hydrobromides and sulphates.

Even more advantageously, according to the present invention, it is preferred to use the following direct dyes:

1-amino-2-nitro-4-N-(β-hydroxyethyl)amino-5-methylbenzene, 1,4,5,8-tetraaminoanthraquinone 1,4-bis-N,N'-[(β, γ-dihydroxypropyl)amino]-anthraquinone 1,4,4-N-tris(β-hydroxyethyl)-1,4-diamino-2-nitrobenzene, 1-N-(β-hydroxyethyl)amino-2-nitro-4-aminobenzene, 1-hydroxy-3-nitro-4-aminobenzene, 1-hydroxy-3-nitro-4-N-(β-hydroxyethyl)aminobenzene, 1-(β-hydroxyethyloxy-3-methylamino-4-nitrobenzene, 1-methylamino-2-nitro-5-β, γ-dihydroxypropyloxy-benzene, 4-[N-ethyl-N-(β-hydroxyethyl)amino]-1-N-(β-hydroxyethyl)amino-2-nitrobenzene, 1-4'-amino-diphenylazo)-2-methyl-4-N-bis(β-hydroxyethylaminobenzene, 1-methoxy-3-N-(β-aminoethyl)amino-4-nitrobenzene 1-amino-2-nitro-4-N-(β-hydroxyethyl)aminobenzene, 1-amino-2-nitro-4-N-bis(β-hydroxyethyl)aminobenzene, 1,4-N-bis(β-hydroxyethyl)amino-5-nitrobenzene, 1,4-diaminoanthraquinone, and the cosmetically acceptable salts thereof.

Other preferred cationic dyes are those such as Arianor (Basic Brown 17, Basic Brown 16, Basic Yellow 57, Basic Blue 99) and the cationic dyes described in CIBA patents WO 95/01772, WO 95/15144 and EP 714,954.

The direct dyes, in basic or salified form, are generally present in the dye composition according to the invention in proportions which can range from about 0.001 to about 10% and preferably from about 0.05 to about 5% by weight relative to the total weight of the composition.

One subject of the invention is also a process for dyeing keratin fibres, in which as composition for direct dyeing as defined above is applied to these keratin fibres, in an amount which is sufficient to produce a coloration, and this composition is left to act for a period of between 10 and 60 min. approximately. The keratin fibres are then rinsed. It is also possible to carry out direct dyeing operations without rinsing.

The present invention also relates to compositions for the oxidation dyeing of keratin fibres, and in particular human keratin fibres such as the hair, containing, in a medium which is suitable for dyeing, at least one polymer as defined above and at least one oxidation dye precursor and/or melanin precursors.

The oxidation dye precursors can be chosen in particular from para-phenylenediamines, para-aminophenols, ortho-phenylenediamines and heterocyclic bases such as, for example, pyridine derivatives, pyrimidine derivatives, pyrazole derivatives, pyrazolepyrimidine derivatives, indoles or indolines, and the addition salts thereof with acids.

These compositions can also contain couplers which can be chosen in particular from meta-phenylenediamines, meta-aminophenols, meta-diphenols, heterocyclic couplers such as, for example, indole derivatives, indoline derivatives, benzimidazole derivatives, benzomorpholine derivatives, sesamol derivatives, pyridine, pyrimidine and pyrazole derivatives, and the addition salts thereof with an acid.

In general, the addition salts with an acid which can be used in the context of the dye compositions are chosen in particular from the hydrochlorides, hydrobromides, sulphates, citrates, succinates, tartrates, lactates and acetates.

The medium which is suitable for the direct dyeing or oxidation dyeing (or the support) generally consists of water or of a mixture of water and at least one organic solvent to dissolve the compounds which would not be sufficiently soluble in the water.

As organic solvents, mention may be made, for example, of lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

When they are present, the oxidation base(s) preferably represent(s) from 0.0005 to12% by weight approximately relative to the total weight of the dye composition.

When they are present, the coupler(s) preferably represents) from 0.0001 to 10% by weight approximately relative to the total weight of the dye composition.

The polymers of the invention preferably represent from 0.01 to 10% by weight approximately relative to the total weight of the direct dye composition or oxidizing composition, and preferably from 0.1 to 5%.

The solvents can be present in proportions preferably of between 1 and 40% by weight approximately relative to the total weight of the dye composition, and even more preferably between 5 and 30% by weight approximately.

The pH of the dye compositions is generally between 3 and 12 approximately and preferably between 5 and 11. It can be adjusted to the desired value using acidifying or basifying agents usually used in the dyeing of keratin fibres.

Among the acidifying agents, mention may be made, for example, of inorganic or organic acids such as hydrochloric acid, orthophosphoric acid, sulphuric acid, carboxylic acids such as acetic acid, tartaric acid, citric acid and lactic acid, and sulphonic acids.

Among the basifying agents, mention may be made, for example, of aqueous ammonia, alkaline carbonates, alkanolamines such as mono-, di- and triethanolamine and derivatives thereof, sodium hydroxide, potassium hydroxide and the compounds of the following formula:

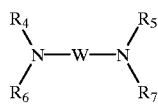

in which W is a propylene residue optionally substituted with a hydroxyl group or a $C_1$–$C_6$ alkyl radical; $R_4$, $R_5$, $R_6$ and $R_7$, which may be identical or different, represent a hydrogen atom or a $C_1$–$C_6$ alkyl or $C_1$–$C_6$ hydroxyalkyl radical.

The dye compositions comprising a polymer of the present invention can also contain various adjuvants conventionally used in compositions for dyeing keratin fibres, such as anionic, cationic, nonionic, amphoteric or zwitterionic surfactants or mixtures thereof, anionic, cationic other than those of the invention, nonionic, amphoteric or zwitterionic polymers or mixtures thereof, inorganic or organic thickeners, antioxidants, penetrating agents, sequestering agents, fragrances, buffers, dispersing agents, conditioners, such as, for example, volatile or non-volatile, modified or unmodified silicones, film-forming agents, ceramides, preserving agents and opacifiers.

The oxidizing compositions used in the oxidation dyeing can also contain a heterocyclic polyquaternary ammonium silicone polymer as defined above and at least one oxidizing agent, and, in this respect, constitute another subject of the invention.

These oxidizing agents can be chosen in particular from hydrogen peroxide, urea peroxide, alkali metal bromates, persalts such as perborates and persulphates, and enzymes such as peroxidases and two-electron oxidoreductases. It is particularly preferred to use hydrogen peroxide or enzymes.

The oxidizing compositions can also contain various adjuvants conventionally used in compositions for dyeing keratin fibres, such as those defined above.

A subject of the invention is also a process for dyeing keratin fibres, in particular the hair, in which an oxidation dye composition as defined above is applied to these keratin fibres, in an amount which is sufficient to dye the keratin fibres, optionally with an oxidizing composition. In the latter case, only the composition containing the dye precursors or the oxidizing composition can contain a polymer according to the invention.

The oxidation dye composition is generally is diluted, at the time of use, with the oxidizing composition in a ratio ranging from 0.5 to 5 and preferably from 1 to 3 volumes. The composition thus obtained is left to act for a period of between 5 and 45 minutes approximately, preferably between 15 and 30 minutes, and the keratin fibres are then rinsed.

The polymers in accordance with the invention are particularly advantageous in their use as protective agents in compositions for bleaching keratin fibres, in particular the hair.

A subject of the present invention is thus also a bleaching composition containing, in a medium which is suitable for bleaching, at least one agent for bleaching keratin fibres, and in particular human hair and at least one polymer as defined above.

The medium which is suitable for bleaching can also contain the same constituents as those of the medium which is suitable for the direct or oxidative dyeing.

The bleaching compositions can also be in the form of powders.

Bleaching agents known per se, such as hydrogen peroxide, persulphates, alkaline percarbonates and perborates, are used for bleaching keratin fibres. Compositions which can contain upto 60 volumes of hydrogen peroxide, and preferably 10 to 40 volumes, are generally used when hydrogen peroxide is used.

Another subject of the invention is a process for bleaching keratin fibres, and in particular human keratin fibres such as the hair, in which a bleaching composition as defined above is applied to the keratin fibres in an amount and for a period which are sufficient to bleach the keratin fibres. The keratin fibres are then washed, rinsed and dried.

The examples which follow are intended to illustrate the invention:

Table 1 below in intended to illustrate the preparation of polymers used according to the invention.

This table successively summarizes the indications relating to the structure of the polymer compound of formula (I).

TABLE 1

| | | | (I) | | | | | | | |
|---|---|---|---|---|---|---|---|---|---|---|
| Ex. | $A_1^{\oplus}$ | $A_2^{\oplus}$ | $B_1$ | $B_2$ | $R_1$ | $R_2$ | p | $R_3$ | $R_4$ | $X^{\ominus}$ |
| Ex. 1 | imidazole of formula (IV) with $R_7 = R_8 = R_9 = H$ | imidazole of formula (IV) with $R_7 = R_8 = R_9 = H$ | $(CH_2)_4$ | $CH_2$ | $CH_3$ | $CH_3$ | 0 | — | — | $Cl^-$ |
| Ex. 2 | imidazole of formula (IV) with $R_7 = R_8 = R_9 = H$ | imidazole of formula (IV) with $R_7 = R_8 = R_9 = H$ | $(CH_2)_4$ | $(CH_2)_3$ | $CH_3$ | $CH_3$ | 1 | $CH_3$ | $CH_3$ | $Cl^-$ |

TABLE 1-continued (I)

| Ex. | $A_1^\oplus$ | $A_2^\oplus$ | $B_1$ | $B_2$ | $R_1$ | $R_2$ | p | $R_3$ | $R_4$ | $X^\ominus$ |
|---|---|---|---|---|---|---|---|---|---|---|
| Ex. 3 | quaternary ammonium of formula (III) with $R_5 = R_6 = CH_3$ | imidazole of formula (IV) with $R_7 = R_8 = R_9 = H$ | $(CH_2)_3$ | $(CH_2)_3$ | $CH_3$ | $CH_3$ | 1 | $CH_3$ | $CH_3$ | $Cl^-$ |
| Ex. 4 | imidazole of formula (IV) with $R_7 = R_8 = R_9 = H$ | imidazole of formula (IV) with $R_7 = R_8 = R_9 = H$ | —CH$_3$—⟨phenyl⟩—CH$_2$— | $(CH_2)_3$ | $CH_3$ | $CH_3$ | 1 | $CH_3$ | $CH_3$ | $Cl^-$ |
| Ex. 5 | imidazole of formula (IV) with $R_7 = R_8 = R_9 = H$ | imidazole of formula (IV) with $R_7 = R_8 = R_9 = H$ | —CH$_3$—⟨phenyl⟩—CH$_2$— | $CH_2$–CHOH–$CH_2$–O–$(CH_2)_3$ | $CH_3$ | $CH_3$ | 8 | $CH_3$ | $CH_3$ | $AcO^-$ |
| Ex. 6 | imidazole of formula (IV) with $R_7 = R_8 = R_9 = H$ | imidazole of formula (IV) with $R_7 = R_8 = R_9 = H$ | —CH$_3$—⟨phenyl⟩—CH$_2$— | $(CH_2)_3$ | $CH_3$ | $CH_3$ | 5 | $CH_3$ | $CH_3$ | $Cl^-$ |

1) Synthesis of Example 1 a) Synthesis of the diamine 1,1'-(1,4-butandiyl)bis(imidazole)

35.4 g (0.52 mol) of imidazole, a solution of 100 g (2.5 mol) of sodium hydroxide in 100 ml of water, 5.15 g of tetrabutylammonium bromide and 54 g (0.26 mol) of 1,4-dibromobutane dissolved in 240 ml of toluene are introduced into a reactor equipped with a mechanical stirrer, a thermometer and a condenser. This mixture is refluxed for 6 hours. After cooling, the expected diamine crystallizes and is filtered off and the filter cake obtained is washed with 100 ml of toluene and then with twice 50 ml of ice-cold water. The product thus washed is recrystallized from 200 ml of water. After drying, 44 g of a pale beige powder are obtained (yield: 89%).

A proton NMR analysis in DMSO gave the following results: $\delta 1.61$–1.68 (m,4H); $\delta 3.96$–4.02 (m,4H); $\delta 6.91$ (m,2H); $\delta 7.17$ (m,2H); $\delta 7.64$ (m,2H)

b) Synthesis of the Polymer

A mixture of 21.09 g (0.1 mol) of 1,1'-(1,4-butanediyl)bis(imidazole) obtained above containing 6.6% water, 30 ml of methanol and 15.7 g (0.1 mol) of bis(chloromethyl)dimethylsilane is maintained at the reflux point of the methanol for 14 hours. Assay of a test sample with silver nitrate shows that 94.6% of the chlorides are in ionic form. The reaction medium is concentrated and dried under vacuum. The very hygroscopic product is placed in water so as to obtain a solution containing 20% active material.

Assay of the chlorides with $AgNO_3$: 1.15 meq $Cl^-/g$ of solution.

2) Synthesis of Example 2

A mixture of 10.5g (0.05 mol) of 1,1'-(1,4-butanediyl)bis(imidazole) containing 6.6% water, 40 ml of methanol and 14.35 g (0.05 mol) of 1,3-bis(chloropropyl)tetramethyldisiloxane is maintained at 120° C. for 38 hours in a hermetically sealed reactor. The reaction medium is concentrated and the residue is then washed with diisopropyl ether and next dried under a vacuum of 0.1 mmHg at 120° C. A water-soluble, vitreous brown-grey polymer is obtained.

Assay of the chlorides with $AgNO_3$: 14.9% (theory: 14.8%).

3) Synthesis of Example 3 a) Synthesis of (3-imidazol-1-ylpropyl)dimethylamine

Dimethylaminochloropropylamine hydrochloride (31.6 g, 0.2 mol), imidazole (13.6 g, 0.2 mol) and tetrabutylammonium bromide (4.4 g) in 100 ml of toluene are introduced into a reactor equipped with a thermometer and a condenser. 80 g of sodium hydroxide dissolved in 80 ml of water are introduced dropwise at a temperature below 50° C. The mixture is left stirring at room temperature for 10 hours. 200 ml of toluene and 50 ml of water are added. The intermediate phase is taken up in dichloromethane and dried. After removing the solvent, the oil obtained is dried under vacuum and is subjected to distillation under a vacuum of 0.1 mm Hg. The fraction distilling at 91–92° C. is (3-imidazol-1-ylpropyl)dimethylamine.

A proton NMR analysis in DMSO gave the following results: $\delta 1.70$ (m,2H); $\delta 1.97$ (t,2H); $\delta 2.00$ (s,6H); $\delta 3.85$ (t,2H); $\delta 6.76$ (m,1H); $\delta 7.05$ (m,1H); $\delta 7.48$ (m,1H).

b) Synthesis of the Polymer in Aqueous Solution

A mixture of 7.66 g (0.05 mol) of 96% N,N-dimethyl-1H-imidazole-1-propanamine, 40 g of methanol and 14.35 g (0.05 mol) of 1,3-bis(chloropropyl)tetramethyldisiloxane is maintained at 120° C. for 28 hours in a hermetically sealed reactor. After cooling, the reaction medium is concentrated. The pale yellow oil obtained is taken up in water and the mixture is concentrated to remove the residual methanol. After assaying the chlorides with $AgNO_3$, the mixture is made up with water to obtain 40.4 g of a solution containing 50% of the polymeric active material.

4) Synthesis of Example 4 a) Synthesis of N,N'-terephthalylidenebis(imidazole)

Sodium hydroxide (32 g, 0.8 mol) in 100 ml of tetrahydrofuran is introduced into a reactor equipped with a thermometer and a condenser, followed by introduction of a solution of imidazole (39.5 g, 0.58 mol) in 300 ml of tetrahydrofuran. After stirring for 40 minutes at room temperature, the initially colourless medium turns orange-pink. This mixture is brought to 60° C. and dichloro-p- xylene (49 g, 0.28 mol) is added portionwise over 25 minutes, and the resulting mixture is then left stirring for 8 hours at 60° C. The reaction mixture, containing an insoluble material, is cooled and 1.4 l of water are then added thereto. The NaCl precipitate dissolves, and then another white precipitate appears.

This precipitate is filtered off. After drying, 49.9 g (yield; 74.8%) of an off-white powder of N,N'-terephthalylidenebis (imidazole) are obtained.

A proton NMR analysis in DMSO gave the following results: δ5.01 (s,4H); δ6.74 (s,2H); δ7.01 (s,2H); δ7.08 (m,4H); δ7.58 (s,2H).

b) Synthesis of the polymer in aqueous solution

A mixture of 7.66 g (0.05 mol) of N,N'-terephthalylidenebis(imidazole), 40 g of methanol and 14.35 g (0.05 mol) of 1,3-bis(chloropropyl)tetramethyl-disiloxane is maintained at 120° C. for 28 hours in a hermetically sealed reactor. After cooling, the reaction medium is concentrated. The pale yellow oil obtained is taken up water and the mixture is concentrated to remove the residual methanol. After assaying the chlorides with $AgNO_3$, the mixture is made up with water in order to obtain 42 g of a solution containing 50% of the polymeric active material.

5) Synthesis of Example 5

α,ω-Diepoxypropoxypropyldiorganodimethylsiloxane (DMS-E12 (p=9) from Gelest, 5 g, 0.005 mol) is added to a solution of N,N'-terephthalylidenebis(imidazole) (1.19 g, 0.005 mol) in 7 g of water and 0.64 g of acetic acid maintained at 60° C. for 20 minutes. 5 ml of isopropanol are added and, after 1 hour, the mixture is transferred into a hermetically sealed reactor and the system is heated at 120° C. for 10 hours. After cooling and evaporation of the solvents, a viscous orange-yellow oil of polymer is obtained, the proton NMR spectrum of which in DMSO is in accordance with the expected formula.

6) Synthesis of Example 6 in aqueous solution

A mixture of 1.13 g (0.01 mol) of N,N'-terephthalylidenebis(imidazole), 20 g of isopropanol and 5.83 g (0.01 mol) of α,ω-chloropropyldodecamethylhexasiloxane is maintained at 120° C. for 20 hours in a hermetically sealed reactor. After cooling, the reaction medium is concentrated. The yellow oil obtained is taken up in water and the mixture is concentrated to remove the residual isopropanol. After assaying the chlorides with $AgNO_3$, the mixture is completed with water in order to obtain 13.5 g of a solution containing 50% polymeric active material.

The examples which follow are intended to illustrate the compositions and the application of the polymers in accordance with the invention.

APPLICATION EXAMPLE 1

The following composition is prepared:

| | |
|---|---|
| 2,6-Dimethyl-1,4-diaminobenzene dihydrochloride | 0.3 g |
| 1-Amino-4-hydroxybenzene | 0.15 g |
| 1,3-Dihydroxybenzene | 0.15 g |
| 1-Hydroxy-3-aminobenzene | 0.1 g |
| tert-Butylhydroxyquinone | 0.04 g |
| Thiolactic acid | 0.4 g |
| Cetyl alcohol and stearyl alcohol as a 50/50 mixture | 17.0 g |
| 2-Octyldodecanol | 2.8 g |
| Cetylstearyl alcohol containing 15 mol of ethylene oxide | 2.8 g |
| Ammonium lauryl sulphate containing 30% A.M. | 11.5 g |

-continued

| | |
|---|---|
| Aqueous solution of the polymer of Example 2 | 3.0 g A.M. |
| Aqueous ammonia at 22° Be | 12.0 g |
| Water qs | 100 g |

This composition is used for the oxidation dyeing of the hair.

The composition obtained is mixed with 1.5 times its weight of 20-volumes aqueous hydrogen peroxide solution of pH 3.

The mixture thus prepared, is applied to dark blonde hair for 30 minutes.

The hair is then rinsed, washed with a standard shampoo and then dried. The hair has a light blonde coloration and feels soft, looks shiny and is easy to disentangle.

APPLICATION EXAMPLE 2

The following composition is prepared:

| | |
|---|---|
| Oleocetyl alcohol oxyethylenated with 30 mol of ethylene oxide | 7 g |
| Lauryl alcohol containing 12 mol of ethylene oxide | 8 g |
| Decyl alcohol containing 3.5 mol of ethylene oxide | 22 g |
| Cetylstearyl alcohol | 5 g |
| Aqueous solution of polymer of Example 2 | 1 g A.M. |
| Propylene glycol | 6 g |
| Aqueous ammonia solution containing 20% $NH_3$ | 10 g |
| para-Phenylenediamine | 0.4 g |
| m-Aminophenol | 0.5 g |
| Hydroquinone | 0.1 g |
| 1-Phenyl-3-methyl-5-pyrazolone | 0.1 g |
| Aqueous sodium bisulphite solution containing 35% A.M. | 1.3 g |
| Fragrance, sequestering agent qs | |
| Water qs | 100 g |

This composition is used for the oxidation dyeing of the hair.

The composition obtained is mixed, weight for weight, with 20-volumes aqueous hydrogen peroxide solution of pH 3.

The mixture thus prepared is then applied to bleached hair for 30 minutes.

The hair is then rinsed, washed with a standard shampoo and then dried.

The hair has a purple coloration and feels soft, looks shiny and is easy to disentangle.

APPLICATION EXAMPLE 3

The following composition is prepared:

| | |
|---|---|
| 2-Amino-5β-hydroxyethyloxynitrobenzene | 0.35 g |
| 2-Amino-4-methyl-5N-β-hydroxyethylamino-nitrobenzene | 0.05 g |
| Nonylphenol containing 9 mol EO | 8 g |
| Lauric diethanolamide | 2 g |
| Aqueous solution of the polymer of Example 2 | 0.8 g A.M. |
| Propylene glycol monomethyl ether | 10 g |
| 2-amino-2-methylpropanol qs | pH 9.5 |
| Demineralized water qs | 100.0 g |

This composition is used for the direct dyeing of the hair.

It is applied for 20 minutes to grey hair containing 90% white hairs.

The hair is then rinsed and dried.

The hair has a golden coppery coloration and feels soft, looks shiny and is easy to disentangle.

What is claimed is:

1. A polymer, comprising at least one unit chosen from units of formula (I):

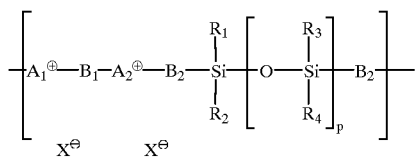

in which:

R$_1$, R$_2$, R$_3$ and R$_4$, which may be identical or different, are chosen from C$_1$ to C$_6$ alkyl groups and phenyl groups;

p is chosen from integers and fractions ranging from 0 to 50;

X$^\ominus$ is chosen from anions derived from halogen inorganic and organic acids; and A$_1^\oplus$, and A$_2^\oplus$, which may be identical or different, are chosen from:

(a) quaternary unsaturated heterocycles of formula (II):

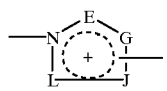

in which:

E, G, L and J, which may be identical or different, are chosen from a carbon atom, an oxygen atom, a sulphur atom and a nitrogen atom, wherein at least one of E, G, L and J is a nitrogen atom;

wherein if at least one of E, G, L and J is a carbon atom, said carbon atom may be unsubstituted or substituted with at least one substituent chosen from halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —NHR$_N$ in which R$_N$ is chosen from a hydrogen atom, alkyl groups, monohydroxyalkyl groups, polyhydroxyalkyl groups, an acetyl group and a ureido group;

wherein if at least two of E, G, L and J are nitrogen atoms, said nitrogen atoms, independent of each other, may be substituted with a hydrogen atom, alkyl groups, monohydroxyalkyl groups, polyhydroxyalkyl groups, substituted aryl radicals, unsubstituted aryl radicals, substituted alkylaryl radicals and unsubstituted alkylaryl radicals; and wherein two substituents of E, G, L and J may form, together with the atoms to which they are attached, a substituted or unsubstituted 5- to 7-member aromatic ring; and (b) quaternary ammoniums of formula (III):

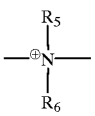

in which:

R$_5$ and R$_6$, which may be identical or different, are chosen from a carboxyl group, alkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —NHR$_N$ in which R$_N$ is an acetyl or ureido group;

R$_5$ and R$_6$ may form, together with the nitrogen atom to which they are attached, a saturated 5- to 7-carbon member ring;

wherein at least one of the groups A$_1^\oplus$, and A$_2^\oplus$ is chosen from the quaternary unsaturated heterocycles of formula (II);

B$_1$ is chosen from α, ω-bis(alkyl)polysiloxane groups and hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted; and B$_2$ is chosen from hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted.

2. A polymer according to claim 1, wherein at least one of A$_1^\oplus$, and A$_2^\oplus$ is chosen from quaternary imidazole groups of formula (IV):

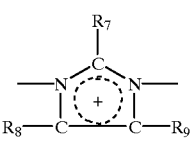

in which:

$R_7$, $R_8$ and $R_9$, which may be identical or different, are chosen from a hydrogen atom, halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups and groups chosen from —$NHR_N$ in which $R_N$ is chosen from a hydrogen atom, alkyl groups, monohydroxyalkyl groups, polyhydroxyalkyl groups, an acetyl group and a ureido group; and wherein the radicals $R_8$ and $R_9$ may form, together with the atoms to which they are attached, 5- to 7-member aromatic rings.

3. A polymer according to claim 2, wherein $A_1^\oplus$ and $A_2^\oplus$ are simultaneously chosen from quaternary imidazole groups of formula (IV), in which:

$R_7$, $R_8$ and $R_9$, which may be identical or different, are chosen from a hydrogen atom, a hydroxyl group, a nitro group, a cyano group, a sulphydryl group, a carboxyl group, alkyl groups, monohydroxyalkyl groups, and polyhydroxyalkyl groups; and wherein $R_8$ and $R_9$ may form, together with the atoms to which they are attached, a 5- to 7-member aromatic ring.

4. A polymer according to claim 2, wherein $A_1^\oplus$, and $A_2^\oplus$ are simultaneously chosen from quaternary imidazole groups of formula (IV), in which:

$R_7$, $R_8$ and $R_9$, which may be identical or different, are chosen from a hydrogen atom, and $C_1$ to $C_6$ alkyl groups, and wherein $R_8$ and $R_9$ may form, together with the atoms to which they are attached, a phenyl ring.

5. A polymer according to claim 2, wherein $A_1^\oplus$, and $A_2^\oplus$ are simultaneously chosen from quaternary imidazole groups of formula (IV), in which:

$R_1$, $R_2$, $R_3$, and $R_4$ are $CH_3$ groups;

$R_7$, $R_8$, $R_9$ are hydrogen atoms;

$B_1$ is chosen from —$(CH_2)_n$— wherein n ranges from 2 to 6 and

$B_2$ is chosen from —$(CH_2)_m$—, wherein m ranges from 1 to 4;

p is chosen from integers ranging from 0 to 4; and $X^\ominus$ is chosen from chloride and bromide anions.

6. A polymer according to claim 1, wherein at least one of $A_1^\ominus$, and $A_2^\oplus$ is chosen from quaternary pyrazole groups of formula (V):

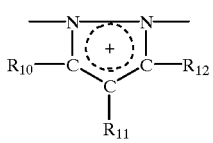

in which:

$R_{10}$, $R_{11}$ and $R_{12}$, which may be identical or different, are chosen from a hydrogen atom, halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups and groups chosen from —$NHR_N$ in which $R_N$ is chosen from a hydrogen atom, alkyl groups, monohydroxyalkyl groups, polyhydroxyalkyl groups, an acetyl group and a ureido group; and wherein two of the radicals $R_{10}$, $R_{11}$, or $R_{12}$ may form, together with the atoms to which they are attached, a 5- to 7-member aromatic ring.

7. A polymer according to claim 1, wherein $A_1^\oplus$ is chosen from quaternary ammoniums of formula (III), in which: $R_5$ and $R_6$, which may be identical or different, are chosen from $C_1$ to $C_6$ alkyl groups, or together form a 6-member ring; and further wherein $A_2^\oplus$ is chosen from quaternary imidazole groups of formula (IV):

in which:

$R_7$, $R_8$ and $R_9$, which may be identical or different, are chosen from a hydrogen atom, $C_1$ to $C_6$ alkyl groups, and wherein $R_8$ and $R_9$ may form, together with the atoms to which they are attached, a phenyl ring.

8. A polymer according to claim 1, wherein $B_1$ is chosen from:

i) —$(CH_2)_n$—, wherein n ranges from 2 to 6;

ii) —$CH_2$—CH=CH—$CH_2$—;

iii) —$CH_2$—C≡C—$CH_2$—;

iv) —$CH(CH_3)$—$(CH_2)_2$—;

v) —$CH_2CHOH$—$CH_2$—;

vi) —$[CH_2-CH_2-O]_x$-, wherein x ranges from 1 to 15;

vii)

viii)

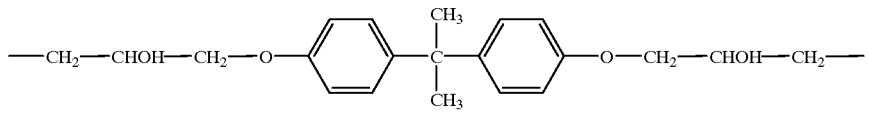

and ix)

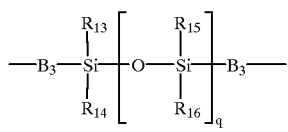

in which:

R$_{13}$, R$_{14}$, R$_{15}$ and R$_{16}$, which may be identical or different, are chosen from C$_1$ to C$_6$ alkyl radicals and a phenyl radical, q is chosen from integers and fractions ranging from 0 to 50, and B$_3$ is chosen from —(CH$_2$)$_t$—, wherein t ranges from 1 to 6, and hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted.

9. A polymer according to claim 1, wherein B$_2$ is —(CH$_2$)$_m$—, wherein m is chosen from integers ranging from 1 to 6.

10. A polymer according to claim 1, wherein R$_1$, R$_2$, R$_3$ and R$_4$ are simultaneously CH$_3$.

11. A cosmetic composition for the cosmetic treatment or protection of keratin fibers, said composition comprising, in a cosmetically acceptable medium, at least one polymer comprising at least one unit chosen from units of formula

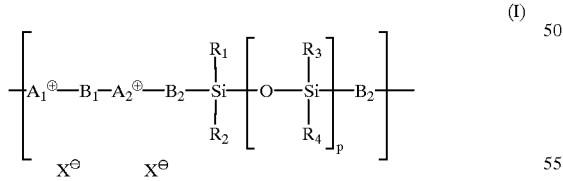

(I)

in which:

R$_1$, R$_2$, R$_3$ and R$_4$, which may be identical or different, are chosen from C$_1$ to C$_6$ alkyl groups and phenyl groups;

p is chosen from integers and fractions ranging from 0 to 50;

X$^\ominus$ is chosen from anions derived from inorganic and organic acids; and

A$_1^\oplus$ and A$_2^\oplus$, which may be identical or different, are chosen from:

(a) quaternary unsaturated heterocycles of formula (II):

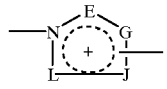

(II)

in which:

E, G, L and J, which may be identical or different, are chosen from a carbon atom, an oxygen atom, a sulphur atom and a nitrogen atom, wherein at least one of E, G, L and J is a nitrogen atom;

wherein if at least one of E, G, L and J is a carbon atom, said carbon atom may be unsubstituted or substituted with at least one substituent chosen from halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —NHR$_N$ in which R$_N$ is chosen from a hydrogen atom, alkyl groups, monohydroxyalkyl groups, polyhydroxyalkyl groups, an acetyl group and a ureido group;

wherein if at least two of E, G, L and J are nitrogen atoms, said nitrogen atoms, independent of each other, may be substituted with a hydrogen atom, alkyl groups, monohydroxyalkyl groups, polyhydroxyalkyl groups, substituted aryl radicals, unsubstituted aryl radicals, substituted alkylaryl radicals and unsubstituted alkylaryl radicals; and wherein two substituents of E, G, L and J may form, together with the atoms to which they are attached, a substituted or unsubstituted 5- to 7-member aromatic ring; and (b) quaternary ammoniums of formula (III):

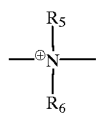

(III)

in which:

R$_5$ and R$_6$, which may be identical or different, are chosen from a carboxyl group, alkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —NHR$_N$ in which R$_N$ is an acetyl or ureido group;

R$_5$ and R$_6$ may form, together with the nitrogen atom to which they are attached, a saturated 5- to 7-carbon member ring;

wherein at least one of the groups $A_1^\oplus$ and $A_2^\oplus$ is chosen from the quaternary unsaturated heterocycles of formula (II);

$B_1$ is chosen from α, ω-bis(alkyl)polysiloxane groups and hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains have no more than six consecutive carbon atoms before being interrupted; and $B_2$ is chosen from hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be noninterrupted or interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted.

12. The cosmetic composition according to claim 11, wherein said keratin fibers are hairs.

13. A cosmetic composition according to claim 11, wherein said hairs are human hairs.

14. A cosmetic composition according to claim 12, wherein said at least one polymer is present in an amount ranging from 0.01% to 10% by weight relative to the total weight of said cosmetic composition.

15. A reducing composition for permanently shaping keratin fibers, comprising, in a medium suitable for permanent waving:

at least one reducing agent; and at least one polymer comprising at least one unit chosen from units of formula (I):

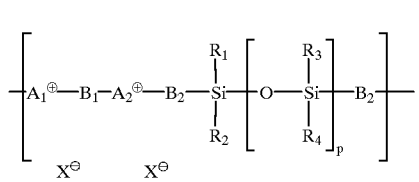

(I)

in which:

$R_1, R_2, R_3$ and $R_4$, which may be identical or different, are chosen from $C_1$ to $C_6$ alkyl groups and phenyl groups;

p is chosen from integers and fractions ranging from 0 to 50;

$X^\ominus$ is chosen from anions derived from inorganic and organic acids; and $A_1^\oplus$ and $A_2^\oplus$, which may be identical or different, are chosen from:

(a) quaternary unsaturated heterocycles of formula (II):

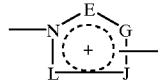

(II)

in which:

E, G, L and J, which may be identical or different, are chosen from a carbon atom, an oxygen atom, a sulphur atom and a nitrogen atom, wherein at least one of E, G, L and J is a nitrogen atom;

wherein if at least one of E, G, L and J is a carbon atom, said carbon atom may be unsubstituted or substituted with at least one substituent chosen from halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is chosen from a hydrogen atom, alkyl groups, monohydroxyalkyl groups, polyhydroxyalkyl groups, an acetyl group and a ureido group;

wherein if at least two of E, G, L and J are nitrogen atoms, said nitrogen atoms, independent of each other, may be substituted with a hydrogen atom, alkyl groups, monohydroxyalkyl groups, polyhydroxyalkyl groups, substituted aryl radicals, unsubstituted aryl radicals, substituted alkylaryl radicals and unsubstituted alkylaryl radicals; and wherein two substituents of E, G, L and J may form, together with the atoms to which they are attached, a substituted or unsubstituted 5- to 7-member aromatic ring; and (b) quaternary ammoniums of formula (III):

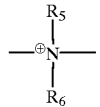

(III)

in which:

$R_5$ and $R_6$, which may be identical or different, are chosen from a carboxyl group, alkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is an acetyl or ureido group;

$R_5$ and R6 may form, together with the nitrogen atom to which they are attached, a saturated 5- to 7-carbon member ring;

wherein at least one of the groups $A_1^\oplus$ and $A_2^\oplus$ is chosen from the quaternary unsaturated heterocycles of formula (II);

$B_1$ is chosen from α, ω-bis(alkyl)polysiloxane groups and hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains have no more than six consecutive carbon atoms before being interrupted; and $B_2$ is chosen from hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be noninterrupted or interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted.

16. A reducing composition according to claim 15, wherein said at least one reducing agent is chosen from sulphites, bisulphites and thiols.

17. A reducing composition according to claim 15, wherein said at least one the reducing agent is chosen from cysteine, cysteamine and cosmetically acceptable salts thereof, thiolactic acid, thioglycolic acid and cosmetically acceptable esters thereof.

18. A reducing composition according to claim 15, wherein said at least one polymer is present in an amount ranging from 0.01 to 10% by weight relative to the weight of said reducing composition.

19. An oxidizing composition for permanently shaping keratin fibers, comprising, in a medium suitable for permanent waving:

at least one oxidizing agent; and at least one polymer comprising at least one unit chosen from units of formula (I):

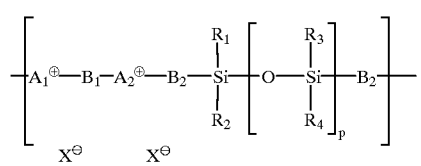

(I)

in which:

$R_1$, $R_2$, $R_3$ and $R_4$, which may be identical or different, are chosen from $C_1$ to $C_6$ alkyl groups and phenyl groups;

p is chosen from integers and fractions ranging from 0 to 50;

$X^\ominus$ is chosen from anions derived from inorganic and organic acids; and $A_1^\oplus$, and $A_2^\oplus$, which may be identical or different, are chosen from:

(a) quaternary unsaturated heterocycles of formula (II):

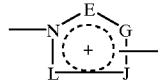

(II)

in which:

E, G, L and J, which may be identical or different, are chosen from a carbon atom, an oxygen atom, a sulphur atom and a nitrogen atom, wherein at least one of E, G, L and J is a nitrogen atom;

wherein if at least one of E, G, L and J is a carbon atom, said carbon atom may be unsubstituted or substituted with at least one substituent chosen from halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is chosen from a hydrogen atom, alkyl groups, monohydroxyalkyl groups, polyhydroxyalkyl groups, an acetyl group and a ureido group;

wherein if at least two of E, G, L and J are nitrogen atoms, said nitrogen atoms, independent of each other, may be substituted with a hydrogen atom, alkyl groups, monohydroxyalkyl groups, polyhydroxyalkyl groups, substituted aryl radicals, unsubstituted aryl radicals, substituted alkylaryl radicals and unsubstituted alkylaryl radicals; and wherein two substituents of E, G, L and J may form, together with the atoms to which they are attached, a substituted or unsubstituted 5- to 7-member aromatic ring; and (b) quaternary ammoniums of formula (III):

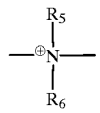

(III)

in which:

$R_5$ and $R_6$, which may be identical or different, are chosen from a carboxyl group, alkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is an acetyl or ureido group;

$R_5$ and $R_6$ may form, together with the nitrogen atom to which they are attached, a saturated 5- to 7-carbon member ring;

wherein at least one of the groups $A_1^\oplus$ and $A_2^\oplus$ is chosen from the quaternary unsaturated heterocycles of formula (II);

$B_1$ is chosen from α, ω-bis(alkyl)polysiloxane groups and hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains have no more than six consecutive carbon atoms before being interrupted; and $B_2$ is chosen from hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be noninterrupted or interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted.

20. An oxidizing composition according to claim 19, wherein said at least one oxidizing agent is chosen from aqueous hydrogen peroxide solutions, urea peroxides, bromates, and persalts.

21. An oxidizing composition according to claim 20, wherein said bromates are chosen from alkaline bromates.

22. An oxidizing composition according to claim 20, wherein said at least one oxidizing agent is a mixture of at least one alkaline bromate and at least one persalt.

23. An oxidizing composition according to claim 19, wherein said at least one polymer is present in an amount ranging from 0.01 to 10% by weight relative to the total weight of said oxidizing composition.

24. A process for permanently shaping keratin fibers, comprising:

applying at least one reducing composition to said keratin fibers;

leaving said reducing composition on said keratin fibers for a period of time sufficient to reduce said keratin;

then applying at least one oxidizing composition to said keratin fibers;

leaving said oxidation composition on said keratin fibers for a period of time sufficient to fix said keratin fibers in a permanent shape; and then rinsing said keratin fibers;

wherein said at least one reducing composition comprises at least one reducing agent;

wherein said at least one oxidizing composition comprises at least one oxidizing agent; and wherein at least one of said at least one reducing composition and at least one oxidizing composition comprises at least one polymer comprising at least one unit chosen from units of formula (I):

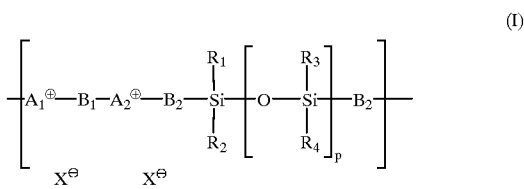

in which:

$R_1$, $R_2$, $R_3$ and $R_4$, which may be identical or different, are chosen from $C_1$ to $C_6$ alkyl groups and phenyl groups;

p is chosen from integers and fractions ranging from 0 to 50;

$X^{\ominus}$ is chosen from anions derived from inorganic and organic acids; and $A_1^{\oplus}$ and $A_2^{\oplus}$, which may be identical or different, are chosen from:

(a) quaternary unsaturated heterocycles of formula (II):

in which:

E, G, L and J, which may be identical or different, are chosen from a carbon atom, an oxygen atom, a sulphur atom and a nitrogen atom, wherein at least one of E, G, L and J is a nitrogen atom;

wherein if at least one of E, G, L and J is a carbon atom, said carbon atom may be unsubstituted or substituted with at least one substituent chosen from halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is chosen from a hydrogen atom, alkyl groups, monohydroxyalkyl groups, polyhydroxyalkyl groups, an acetyl group and a ureido group;

wherein if at least two of E, G, L and J are nitrogen atoms, said nitrogen atoms, independent of each other, may be substituted with a hydrogen atom, alkyl groups, monohydroxyalkyl groups, polyhydroxyalkyl groups, substituted aryl radicals, unsubstituted aryl radicals, substituted alkylaryl radicals and unsubstituted alkylaryl radicals; and wherein two substituents of E, G, L and J may form, together with the atoms to which they are attached, a substituted or unsubstituted 5- to 7-member aromatic ring; and (b) quaternary ammoniums of formula (III):

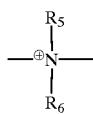
(III)

in which:
R$_5$ and R$_6$, which may be identical or different, are chosen from a carboxyl group, alkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —NHR$_N$ in which R$_N$ is an acetyl or ureido group;

R$_5$ and R$_6$ may form, together with the nitrogen atom to which they are attached, a saturated 5- to 7-carbon member ring;

wherein at least one of the groups A$_1^\oplus$ and A$_2^\oplus$ is chosen from the quaternary unsaturated heterocycles of formula (II);

B$_1$ is chosen from α, ω-bis(alkyl)polysiloxane groups and hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains have no more than six consecutive carbon atoms before being interrupted; and B$_2$ is chosen from hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be noninterrupted or interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted.

25. A process according to claim 24, wherein said keratin fibers are rinsed with water.

26. A composition for direct dyeing of keratin fibers, comprising at least one direct dye and at least one polymer comprising at least one unit chosen from units of formula (I):

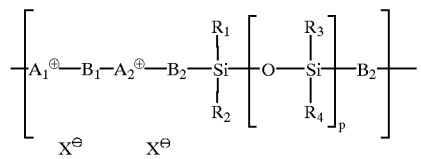
(I)

in which:
R$_1$, R$_2$, R$_3$ and R$_4$, which may be identical or different, are chosen from C$_1$ to C$_6$ alkyl groups and phenyl groups;

p is chosen from integers and fractions ranging from 0 to 50;

X$^\ominus$ is chosen from anions derived from inorganic and organic acids; and

A$_1^\oplus$ and A$_2^\oplus$, which may be identical or different, are chosen from:
(a) quaternary unsaturated heterocycles of formula (II):

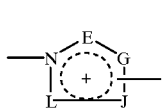
(II)

in which:
E, G, L and J, which may be identical or different, are chosen from a carbon atom, an oxygen atom, a sulphur atom and a nitrogen atom, wherein at least one of E, G, L and J is a nitrogen atom;

wherein if at least one of E, G, L and J is a carbon atom, said carbon atom may be unsubstituted or substituted with at least one substituent chosen from halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —NHR$_N$ in which R$_N$ is chosen from a hydrogen atom, alkyl groups, monohydroxyalkyl groups, polyhydroxyalkyl groups, an acetyl group and a ureido group;

wherein if at least two of E, G, L and J are nitrogen atoms, said nitrogen atoms, independent of each other, may be substituted with a hydrogen atom, alkyl groups, monohydroxyalkyl groups, polyhydroxyalkyl groups, substituted aryl radicals, unsubstituted aryl radicals, substituted alkylaryl radicals and unsubstituted alkylaryl radicals; and wherein two substituents of E, G, L and J may form, together with the atoms to which they are attached, a substituted or unsubstituted 5- to 7-member aromatic ring; and (b) quaternary ammoniums of formula (III):

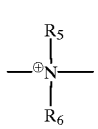
(III)

in which:
R$_5$ and R6, which may be identical or different, are chosen from a carboxyl group, alkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —NHR$_N$ in which R$_N$ is an acetyl or ureido group;

R$_5$ and R$_6$ may form, together with the nitrogen atom to which they are attached, a saturated 5- to 7-carbon member ring;

wherein at least one of the groups $A_1^\oplus$ and $A_2^\oplus$ is chosen from the quaternary unsaturated heterocycles of formula (II);

$B_1$ is chosen from α, ω-bis(alkyl)polysiloxane groups and hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains have no more than six consecutive carbon atoms before being interrupted; and B2 is chosen from hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be noninterrupted or interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted.

27. A composition according to claim 26, wherein said keratin fibers are hairs.

28. A composition according to claim 27, wherein said hairs are human hairs.

29. A composition according to claim 26, further comprising water, at least one organic solvent or a mixture thereof.

30. A composition according to claim 26, wherein said at least one direct dye is chosen from nitrobenzene dyes, azo dyes, anthraquinone dyes, triarylmethane dyes, azine dyes, acridine dyes, xanthene dyes and metal-containing dyes.

31. A composition according to claim 26, wherein said at least one polymer is present in an amount ranging from 0.01% to 10% by weight of said composition.

32. A process for coloring keratin fibers, comprising applying to said keratin fibers a composition comprising at least one direct dye and at least one polymer, wherein said composition is applied to said keratin fibers in an amount sufficient to produce a coloration and is left to act on said keratin fibers for a period of time ranging from about 10 to about 60 minutes, and wherein said at least one polymer comprises at least one unit chosen from units of formula (I):

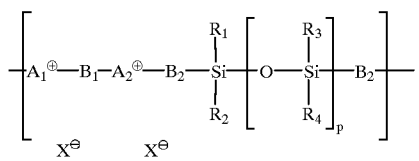

in which:
$R_1, R_2, R_3$ and $R_4$, which may be identical or different, are chosen from $C_1$ to $C_6$ alkyl groups and phenyl groups;
p is chosen from integers and fractions ranging from 0 to 50;
$X^\ominus$ is chosen from anions derived from inorganic and organic acids; and $A_1^\oplus$ and $A_2^\oplus$, which may be identical or different, are chosen from:
(a) quaternary unsaturated heterocycles of formula (II): in which:

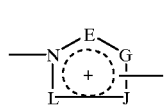

in which:
E, G, L and J, which may be identical or different, are chosen from a carbon atom, an oxygen atom, a sulphur atom and a nitrogen atom, wherein at least one of E, G, L and J is a nitrogen atom;
wherein if at least one of E, G, L and J is a carbon atom, said carbon atom may be unsubstituted or substituted with at least one substituent chosen from halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is chosen from a hydrogen atom, alkyl groups, monohydroxyalkyl groups, polyhydroxyalkyl groups, an acetyl group and a ureido group;
wherein if at least two of E, G, L and J are nitrogen atoms, said nitrogen atoms, independent of each other, may be substituted with a hydrogen atom, alkyl groups, monohydroxyalkyl groups, polyhydroxyalkyl groups, substituted aryl radicals, unsubstituted aryl radicals, substituted alkylaryl radicals and unsubstituted alkylaryl radicals; and
wherein two substituents of E, G, L and J may form, together with the atoms to which they are attached, a substituted or unsubstituted 5- to 7-member aromatic ring; and
(b) quaternary ammoniums of formula (III):

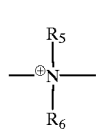

in which:
$R_5$ and $R_6$, which may be identical or different, are chosen from a carboxyl group, alkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is an acetyl or ureido group;
$R_5$ and $R_6$ may form, together with the nitrogen atom to which they are attached, a saturated 5- to 7-carbon member ring;
wherein at least one of the groups $A_1^\oplus$ and $A_2^\oplus$ is chosen from the quaternary unsaturated heterocycles of formula (II);

B₁ is chosen from α, ω-bis(alkyl)polysiloxane groups and hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains have no more than six consecutive carbon atoms before being interrupted; and B₂ is chosen from hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be noninterrupted or interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted.

33. A process according to claim 32, wherein said keratin fibers are hairs.

34. A process according to claim 33, wherein said hairs are human hairs.

35. A process according to claim 32, wherein said period of time ranges from 10 to 60 minutes.

36. A process according to claim 32, further comprising rinsing said keratin fibers.

37. A composition for oxidation dyeing of keratin fibers, comprising at least one precursor chosen from an oxidation dye precursors and melanin precursors, and at least one polymer comprising at least one unit chosen from units of formula (I):

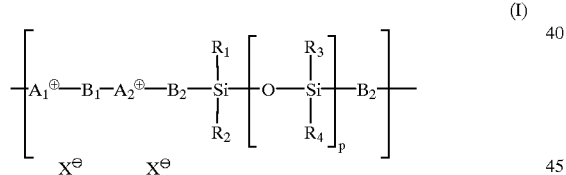

(I)

in which:

R₁, R₂, R₃ and R₄, which may be identical or different, are chosen from $C_1$ to $C_6$ alkyl groups and phenyl groups;

p is chosen from integers and fractions ranging from 0 to 50;

$X^{\ominus}$ is chosen from anions derived from inorganic and organic acids; and $A_1^{\oplus}$ and $A_2^{\oplus}$, which may be identical or different, are chosen from:

(a) quaternary unsaturated heterocycles of formula (II):

(II)

in which:

E, G, L and J, which may be identical or different, are chosen from a carbon atom, an oxygen atom, a sulphur atom and a nitrogen atom, wherein at least one of E, G, L and J is a nitrogen atom;

wherein if at least one of E, G, L and J is a carbon atom, said carbon atom may be unsubstituted or substituted with at least one substituent chosen from halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —NHR$_N$ in which R$_N$ is chosen from a hydrogen atom, alkyl groups, monohydroxyalkyl groups, polyhydroxyalkyl groups, an acetyl group and a ureido group;

wherein if at least two of E, G, L and J are nitrogen atoms, said nitrogen atoms, independent of each other, may be substituted with a hydrogen atom, alkyl groups, monohydroxyalkyl groups, polyhydroxyalkyl groups, substituted aryl radicals, unsubstituted aryl radicals, substituted alkylaryl radicals and unsubstituted alkylaryl radicals; and wherein two substituents of E, G, L and J may form, together with the atoms to which they are attached, a substituted or unsubstituted 5- to 7-member aromatic ring; and (b) quaternary ammoniums of formula (III):

(III)

in which:

R₅ and R₆, which may be identical or different, are chosen from a carboxyl group, alkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —NHR$_N$ in which R$_N$ is an acetyl or ureido group;

R₅ and R₆ may form, together with the nitrogen atom to which they are attached, a saturated 5- to 7-carbon member ring;

wherein at least one of the groups $A_1^{\oplus}$ and $A_2^{\oplus}$ is chosen from the quaternary unsaturated heterocycles of formula (II);

B₁ is chosen from α, ω-bis(alkyl)polysiloxane groups and hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains have no more than six consecutive carbon atoms before being interrupted; and B₂ is chosen from hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be noninterrupted or interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted.

38. A composition according to claim 37, wherein said keratin fibers are hairs.

39. A composition according to claim 38, wherein said hairs are human hairs.

40. A composition according to claim 37, further comprising water, at least one organic solvent or a mixture thereof.

41. A composition according to claim 37, wherein said at least one oxidation dye precursor is chosen from para-phenylenediamines, para-aminophenols, ortho-phenylenediamines, heterocyclic bases and acid addition salts, of any of said precursors.

42. A composition according to claim 37, further comprising at least one coupler.

43. A composition according to claim 42, wherein said at least one coupler is chosen from meta-phenylenediamines, meta-aminophenols, meta-diphenols, heterocyclic compounds, indoline compounds, benzimidazole compounds, benzomorpholine compounds, sesamol compounds, pyridine, pyrimidine, pyrazole compounds and acid addition salts of any of said couplers.

44. A composition according to claims 37, wherein said at least one polymer is present in an amount ranging from 0.01% to 10% by weight of said composition.

45. An oxidizing composition for oxidation dyeing of keratin fibers, comprising, in a medium suitable for dyeing, at least one oxidizing agent and at least one polymer comprising at least one unit chosen from units of formula (I):

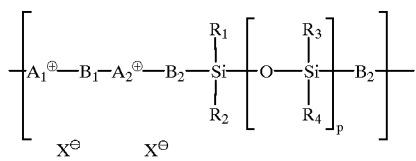

(I)

in which:

$R_1$, $R_2$, $R_3$ and $R_4$, which may be identical or different, are chosen from $C_1$ to $C_6$ alkyl groups and phenyl groups;

p is chosen from integers and fractions ranging from 0 to 50;

$X^\ominus$ is chosen from anions derived from inorganic and organic acids; and $A_1^\oplus$ and $A_2^\oplus$ which may be identical or different, are chosen from:

(a) quaternary unsaturated heterocycles of formula (II):

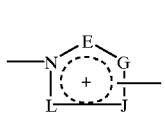

(II)

in which:

E, G, L and J, which may be identical or different, are chosen from a carbon atom, an oxygen atom, a sulphur atom and a nitrogen atom, wherein at least one of E, G, L and J is a nitrogen atom;

wherein if at least one of E, G, L and J is a carbon atom, said carbon atom may be unsubstituted or substituted with at least one substituent chosen from halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is chosen from a hydrogen atom, alkyl groups, monohydroxyalkyl groups, polyhydroxyalkyl groups, an acetyl group and a ureido group;

wherein if at least two of E, G, L and J are nitrogen atoms, said nitrogen atoms, independent of each other, may be substituted with a hydrogen atom, alkyl groups, monohydroxyalkyl groups, polyhydroxyalkyl groups, substituted aryl radicals, unsubstituted aryl radicals, substituted alkylaryl radicals and unsubstituted alkylaryl radicals; and wherein two substituents of E, G, L and J may form, together with the atoms to which they are attached, a substituted or unsubstituted 5- to 7-member aromatic ring; and (b) quaternary ammoniums of formula (III):

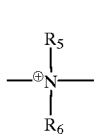

(III)

in which:

$R_5$ and $R_6$, which may be identical or different, are chosen from a carboxyl group, alkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is an acetyl or ureido group;

$R_5$ and $R_6$ may form, together with the nitrogen atom to which they are attached, a saturated 5- to 7-carbon member ring;

wherein at least one of the groups $A_1^\oplus$ and $A_2^\oplus$ is chosen from the quaternary unsaturated heterocycles of formula (II);

$B_1$ is chosen from α, ω-bis(alkyl)polysiloxane groups and hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains have no more than six consecutive carbon atoms before being interrupted; and $B_2$ is chosen from hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be noninterrupted or interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted.

46. An oxidizing composition according to claim 45, wherein said medium suitable for dyeing is water, at least one an organic solvent or a mixture thereof.

47. An oxidizing composition according to claim 45, wherein in said at least one oxidizing agent is chosen from hydrogen peroxide, urea peroxide, alkali metal bromates, persalts, and enzymes.

48. An oxidizing composition according to claim 47, wherein said persalts are chosen from perborates and persulphates.

49. An oxidizing composition according to claim 47, wherein said enzymes are chosen from peroxidases and two-electron oxidoreductases.

50. A process for the cosmetic treatment or protection of keratin fibers, comprising applying to said keratin fibers a cosmetic composition comprising, in a cosmetically acceptable medium, at least one polymer comprising at least one unit chosen from units of formula (I):

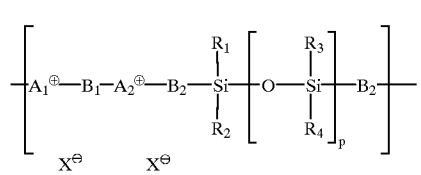

(I)

in which:

$R_1$, $R_2$, $R_3$ and $R_4$, which may be identical or different, are chosen from $C_1$ to $C_6$ alkyl groups and phenyl groups;

p is chosen from integers and fractions ranging from 0 to 50;

$X^\ominus$ is chosen from anions derived from inorganic and organic acids; and $A_1^\oplus$ and $A_2^\oplus$, which may be identical or different, are chosen from:

(a) quaternary unsaturated heterocycles of formula (II):

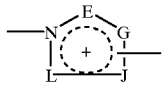

(II)

in which:

E, G, L and J, which may be identical or different, are chosen from a carbon atom, an oxygen atom, a sulphur atom and a nitrogen atom, wherein at least one of E, G, L and J is a nitrogen atom;

wherein if at least one of E, G, L and J is a carbon atom, said carbon atom may be unsubstituted or substituted with at least one substituent chosen from halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is chosen from a hydrogen atom, alkyl groups, monohydroxyalkyl groups, polyhydroxyalkyl groups, an acetyl group and a ureido group;

wherein if at least two of E, G, L and J are nitrogen atoms, said nitrogen atoms, independent of each other, may be substituted with a hydrogen atom, alkyl groups, monohydroxyalkyl groups, polyhydroxyalkyl groups, substituted aryl radicals, unsubstituted aryl radicals, substituted alkylaryl radicals and unsubstituted alkylaryl radicals; and wherein two substituents of E, G, L and J may form, together with the atoms to which they are attached, a substituted or unsubstituted 5- to 7-member aromatic ring; and (b) quaternary ammoniums of formula (III):

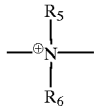

(III)

in which:

$R_5$ and $R_6$, which may be identical or different, are chosen from a carboxyl group, alkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is an acetyl or ureido group;

$R_5$ and $R_6$ may form, together with the nitrogen atom to which they are attached, a saturated 5- to 7-carbon member ring;

wherein at least one of the groups $A_1^\oplus$ and $A_2^\oplus$ is chosen from the quaternary unsaturated heterocycles of formula (II);

$B_1$ is chosen from α, ω-bis(alkyl)polysiloxane groups and hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains have no more than six consecutive carbon atoms before being interrupted; and $B_2$ is chosen from hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be noninterrupted or interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted.

51. A process according to claim 50 wherein said keratin fibers are hairs.

52. A process according to claim 51, wherein said hairs are human hairs.

53. A process for oxidation dyeing of keratin fibers, comprising:
applying to said keratin fibers an oxidation dyeing composition in an amount sufficient to dye said keratin fibers, said oxidation dyeing composition comprising at least one dye precursor, wherein, at the time of application, said oxidation dyeing composition is mixed with an oxidizing composition; and
leaving said oxidation dyeing composition on said keratin fibers for a period of time ranging from 5 to 45 minutes;
wherein said at least one dye precursor is chosen from oxidation dye precursors and melanin precursors;
wherein said oxidizing composition comprises at least one oxidizing agent; and
wherein at least one of said at least one composition for oxidation dyeing of keratin fibers and at least one oxidizing composition further comprises at least one polymer, wherein said at least one polymer comprising at least one unit chosen from units of formula (I):

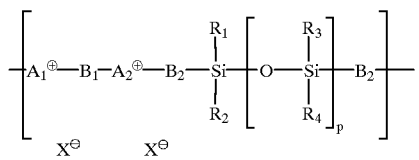

(I)

in which:

$R_1$, $R_2$, $R_3$ and $R_4$, which may be identical or different, are chosen from $C_1$ to $C_6$ alkyl groups and phenyl groups;

p is chosen from integers and fractions ranging from 0 to 50;

$X^\ominus$ is chosen from anions derived from inorganic and organic acids; and $A_1^\oplus$ and $A_2^\oplus$, which may be identical or different, are chosen from:

(a) quaternary unsaturated heterocycles of formula (II):

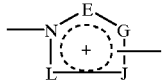

(II)

in which:

E, G, L and J, which may be identical or different, are chosen from a carbon atom, an oxygen atom, a sulphur atom and a nitrogen atom, wherein at least one of E, G, L and J is a nitrogen atom;

wherein if at least one of E, G, L and J is a carbon atom, said carbon atom may be unsubstituted or substituted with at least one substituent chosen from halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is chosen from a hydrogen atom, alkyl groups, monohydroxyalkyl groups, polyhydroxyalkyl groups, an acetyl group and a ureido group;

wherein if at least two of E, G, L and J are nitrogen atoms, said nitrogen atoms, independent of each other, may be substituted with a hydrogen atom, alkyl groups, monohydroxyalkyl groups, polyhydroxyalkyl groups, substituted aryl radicals, unsubstituted aryl radicals, substituted alkylaryl radicals and unsubstituted alkylaryl radicals; and wherein two substituents of E, G, L and J may form, together with the atoms to which they are attached, a substituted or unsubstituted 5- to 7-member aromatic ring; and (b) quaternary ammoniums of formula (III):

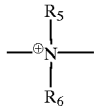

(III)

in which:

$R_5$ and $R_6$, which may be identical or different, are chosen from a carboxyl group, alkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is an acetyl or ureido group;

$R_5$ and $R_6$ may form, together with the nitrogen atom to which they are attached, a saturated 5- to 7-carbon member ring;

wherein at least one of the groups $A_1^\oplus$ and $A_2^\oplus$ is chosen from the quaternary unsaturated heterocycles of formula (II);

$B_1$ is chosen from α, ω-bis(alkyl)polysiloxane groups and hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains have no more than six consecutive carbon atoms before being interrupted; and $B_2$ is chosen from hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be noninterrupted or interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted.

54. A process according to claim 53, further comprising rinsing said keratin fibers.

55. A bleaching composition, comprising, in a medium suitable for bleaching, at least one bleaching agent and at least one polymer comprising at least one unit chosen from units of formula (I):

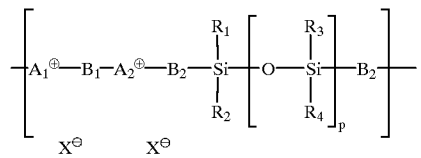

in which:

$R_1$, $R_2$, $R_3$ and $R_4$, which may be identical or different, are chosen from $C_1$ to $C_6$ alkyl groups and phenyl groups;

p is chosen from integers and fractions ranging from 0 to 50;

$X^{\ominus}$ is chosen from anions derived from inorganic and organic acids; and $A_1^{\oplus}$ and $A_2^{\oplus}$, which may be identical or different, are chosen from:

(a) quaternary unsaturated heterocycles of formula (II):

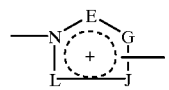

in which:

E, G, L and J, which may be identical or different, are chosen from a carbon atom, an oxygen atom, a sulphur atom and a nitrogen atom, wherein at least one of E, G, L and J is a nitrogen atom;

wherein if at least one of E, G, L and J is a carbon atom, said carbon atom may be unsubstituted or substituted with at least one substituent chosen from halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is chosen from a hydrogen atom, alkyl groups, monohydroxyalkyl groups, polyhydroxyalkyl groups, an acetyl group and a ureido group;

wherein if at least two of E, G, L and J are nitrogen atoms, said nitrogen atoms, independent of each other, may be substituted with a hydrogen atom, alkyl groups, monohydroxyalkyl groups, polyhydroxyalkyl groups, substituted aryl radicals, unsubstituted aryl radicals, substituted alkylaryl radicals and unsubstituted alkylaryl radicals; and wherein two substituents of E, G, L and J may form, together with the atoms to which they are attached, a substituted or unsubstituted 5- to 7-member aromatic ring; and (b) quaternary ammoniums of formula (III):

in which:

$R_5$ and $R_6$, which may be identical or different, are chosen from a carboxyl group, alkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —$NHR_N$ in which $R_N$ is an acetyl or ureido group;

$R_5$ and $R_6$ may form, together with the nitrogen atom to which they are attached, a saturated 5- to 7-carbon member ring;

wherein at least one of the groups $A_1^{\oplus}$ and $A_2^{\oplus}$ is chosen from the quaternary unsaturated heterocycles of formula (II);

$B_1$ is chosen from α, ω-bis(alkyl)polysiloxane groups and hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains have no more than six consecutive carbon atoms before being interrupted; and $B_2$ is chosen from hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be noninterrupted or interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted.

56. A bleaching composition according to claim 55, wherein said at least one bleaching agent is chosen from hydrogen peroxide, persulphates, sodium percarbonates and perborates.

57. A process for bleaching keratin fibers, comprising applying a bleaching composition to keratin fibers in an amount sufficient to bleach said keratin fibers, waiting for a period of time sufficient to bleach said keratin fibers, and rinsing said keratin fibers, wherein said at least one bleaching composition comprises, in a medium suitable for bleaching, at least one bleaching agent and at least one polymer comprising at least one unit chosen from units of formula (I):

in which:
R$_1$, R$_2$, R$_3$ and R$_4$, which may be identical or different, are chosen from C$_1$ to C$_6$ alkyl groups and phenyl groups;
p is chosen from integers and fractions ranging from 0 to 50;
X$^\ominus$ is chosen from anions derived from inorganic and organic acids; and
A$_1^\oplus$ and A$_2^\oplus$, which may be identical or different, are chosen from:
(a) quaternary unsaturated heterocycles of formula (II):

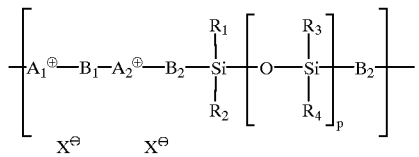

in which:
E, G, L and J, which may be identical or different, are chosen from a carbon atom, an oxygen atom, a sulphur atom and a nitrogen atom, wherein at least one of E, G, L and J is a nitrogen atom;
wherein if at least one of E, G, L and J is a carbon atom, said carbon atom may be unsubstituted or substituted with at least one substituent chosen from halogen atoms, a hydroxyl group, a nitro group, a cyano group, a sulphydryl group, a carboxyl group, alkyl groups, monohydroxyalkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —NHR$_N$ in which R$_N$ is chosen from a hydrogen atom, alkyl groups, monohydroxyalkyl groups, polyhydroxyalkyl groups, an acetyl group and a ureido group;
wherein if at least two of E, G, L and J are nitrogen atoms, said nitrogen atoms, independent of each other, may be substituted with a hydrogen atom, alkyl groups, monohydroxyalkyl groups, polyhydroxyalkyl groups, substituted aryl radicals, unsubstituted aryl radicals, substituted alkylaryl radicals and unsubstituted alkylaryl radicals; and
wherein two substituents of E, G, L and J may form, together with the atoms to which they are attached, a substituted or unsubstituted 5- to 7-member aromatic ring; and
(b) quaternary ammoniums of formula (III):

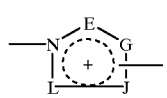

in which:
R$_5$ and R$_6$, which may be identical or different, are chosen from a carboxyl group, alkyl groups, polyhydroxyalkyl groups, thioalkyl groups, cyanoalkyl groups, alkoxy groups, acyl groups, acetyloxy groups, substituted cycloalkyl groups, unsubstituted cycloalkyl groups, substituted aryl groups, unsubstituted aryl groups, substituted alkylaryl groups, unsubstituted alkylaryl groups, and groups chosen from —NHR$_N$ in which R$_N$ is an acetyl or ureido group;
R$_5$ and R$_6$ may form, together with the nitrogen atom to which they are attached, a saturated 5- to 7-carbon member ring;
wherein at least one of the groups A$_1^\oplus$ and A$_2^\oplus$ is chosen from the quaternary unsaturated heterocycles of formula (II);
B$_1$ is chosen from α, ω-bis(alkyl)polysiloxane groups and hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be interrupted, symmetrically or asymmetrically, with at least one oxygen atom and/or at least one aromatic ring, wherein, when said chains are interrupted with at least one oxygen atom and/or at least one aromatic ring, said chains have no more than six consecutive carbon atoms before being interrupted; and
B$_2$ is chosen from hydrocarbon-based chains, wherein said hydrocarbon-based chains may be linear or branched, saturated or unsaturated, and wherein said hydrocarbon-based chains contain carbon atoms which may be unsubstituted or substituted with at least one hydroxyl group and which may be noninterrupted or interrupted, symmetrically or asymmetrically, with at least one oxygen atom and/or at least one aromatic ring, wherein, when said chains are interrupted with at least one oxygen atom and/or at least one aromatic ring, said chains can have no more than six consecutive carbon atoms before being interrupted.

* * * * *

UNITED STATES PATENT AND TRADEMARK OFFICE
CERTIFICATE OF CORRECTION

PATENT NO. : 6,240,929 B1
DATED : June 5, 2001
INVENTOR(S) : Hervé Richard et al.

It is certified that error appears in the above-identified patent and that said Letters Patent is hereby corrected as shown below:

Column 21,
Line 54, "A,$^{\ominus}$" should read -- A,$^{\oplus}$ --.

Column 22,
Line 56, remove comma after subscript "x" and insert -- $CH_2 - CH_2$-, --.

Column 34,
Line 4, delete "in which".

Signed and Sealed this

Fifth Day of August, 2003

JAMES E. ROGAN
*Director of the United States Patent and Trademark Office*